(12) United States Patent
Wang et al.

(10) Patent No.: US 9,347,143 B2
(45) Date of Patent: May 24, 2016

(54) MEMBRANE TEMPLATE SYNTHESIS OF MICROTUBE ENGINES

(75) Inventors: Joseph Wang, San Diego, CA (US); Wei Gao, La Jolla, CA (US); Sirilak Sattayasamitsathit, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 44 days.

(21) Appl. No.: 14/118,891

(22) PCT Filed: Jun. 4, 2012

(86) PCT No.: PCT/US2012/000269
§ 371 (c)(1),
(2), (4) Date: Feb. 18, 2014

(87) PCT Pub. No.: WO2012/166215
PCT Pub. Date: Dec. 6, 2012

(65) Prior Publication Data
US 2014/0162870 A1    Jun. 12, 2014

Related U.S. Application Data

(60) Provisional application No. 61/492,782, filed on Jun. 2, 2011.

(51) Int. Cl.
| | | |
|---|---|---|
| *B01J 23/00* | (2006.01) |
| *B01J 23/40* | (2006.01) |
| *B01J 23/42* | (2006.01) |
| *C25D 1/02* | (2006.01) |
| *B82Y 30/00* | (2011.01) |
| *F03H 99/00* | (2009.01) |

(52) U.S. Cl.
CPC . *C25D 1/02* (2013.01); *B82Y 30/00* (2013.01); *F03H 99/00* (2013.01)

(58) Field of Classification Search
USPC .................................. 502/326, 300, 325
See application file for complete search history.

(56) References Cited

U.S. PATENT DOCUMENTS

| | | |
|---|---|---|
| 2008/0156654 A1 | 7/2008 | Wang et al. |
| 2010/0129656 A1 | 5/2010 | Zussman et al. |
| 2014/0045179 A1* | 2/2014 | Wang ............... G01N 33/54313 435/6.11 |

OTHER PUBLICATIONS

Byun, S.C., Authorized Officer, Korean Intellectual Property Office, International Application No. PCT/US2012/000269, Nov. 23, 2012, 8 pages.
Campuzano, S. et al., "Bacterial Isolation by Lectin-Modified Microengines", Nano Letters, 2012, 12, 396-401.
Cui et al., "A general approach to elecgtrochemical deposition of high quality free-standing noble metal (Pd, Pt, Au, Ag) sub-micron tubes composed of nanoparticles in polar aprotic solvent", Commun. 2010, 46, 940-942.

(Continued)

*Primary Examiner* — James McDonough
(74) *Attorney, Agent, or Firm* — Perkins Coie LLP

(57) ABSTRACT

Methods, structures, devices and systems are disclosed for fabrication of microtube engines using membrane template electrodeposition. Such nanomotors operate based on bubble-induced propulsion in biological fluids and salt-rich environments. In one aspect, fabricating microengines includes depositing a polymer layer on a membrane template, depositing a conductive metal layer on the polymer layer, and dissolving the membrane template to release the multilayer microtubes.

24 Claims, 16 Drawing Sheets

(56) References Cited

OTHER PUBLICATIONS

Gao, W. et al., "Highly Efficient Catalytic Microengines: Template Electrosynthesis of Polyaniline/Platinum Microtubes", J. Am. Chem. Soc., Jul. 2011, vol. 133, No. 31, pp. 11862-11864.

Gao, W. et al., "Hydrogen-Bubble-Propelled Zinc-Based Microrockets in Strongly Acidic Media", JACS, 2012, 134, 897-900.

Gao, W. et al., "Polymer-based tubular microbots: role of composition and preparation", Nanoscale, 2012, 4, 2447.

Gao, W., et al., "Catalytically Propelled Micro-/Nanomotors: How Fast Can They Move?", The Chemical Record, vol. 12, 2012, 224-231.

Guix, M. et al., "Superhydrophobic Alkanethiol-Coated Microsubmarines for Effective Removal of Oil", American Chemical Society, 2010, 7 pages.

Huang, G. et al., "Material considerations and locomotive capability in catalytic tubular microengines", Journal of Materials Chemistry, 2012, 22, 6519.

Lahav, M. et al., "Core-Shell and Segmented Polymer-Metal Composite Nanostructures", Nano Letters, 2006, vol. 6, No. 9, pp. 2166-2171.

Mallouk et al., "Powering Nanorobots", Sci Amer. 2009, 300, 72-77.

Manesh, K.M. et al., "Template-Assisted Fabrication of Salt-Independent Catalytic Tubular Microengines", ACS Nano, 2010, vol. 4, No. 4, pp. 1799-1804.

Martin, "Template Synthesis of Electronically Conductive Polymer Nanostructures", Acc. Chem. Res. 1995, 28, 51-68.

Mei, Y. et al., "Rolled-up nanotech on polymers: from basic perception to self-propelled catalytic microengines", Chem. Soc. Rev., 2011 40, 2109-2119.

Sanchez et al., "Controlled manipulation of multiple cells using catalytic microbots", Chem. Commun. 2009, 47, 698-700.

Solovev, A. A. et al., "Catalytic Microtubular Jet Engines Self-Propelled by Accumulated Bas Bubbles", Small 2009, 5, 1688-1692.

Wang, "Can Man-Made Nanomachines Compete with Nature Biomotors?", ACS Nano 2009, 3, 4-9.

* cited by examiner

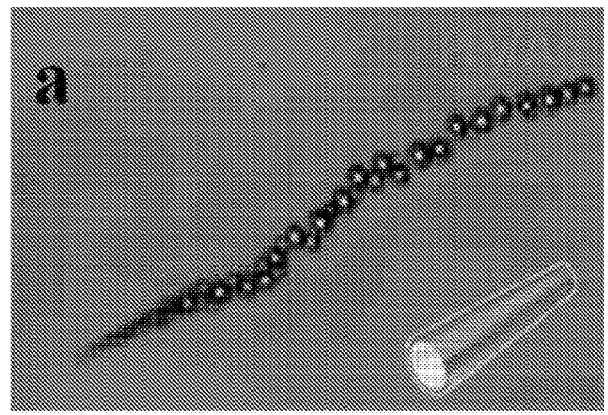
FIG. 25A
FIG. 25B
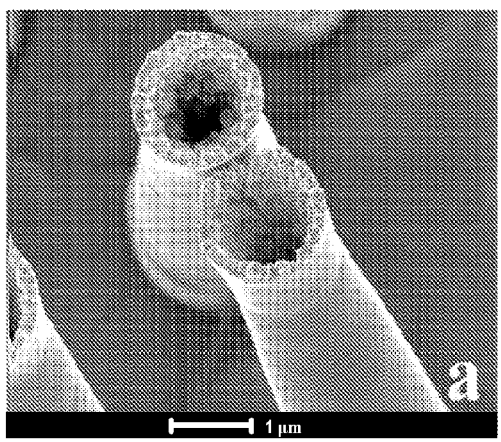
FIG. 26A
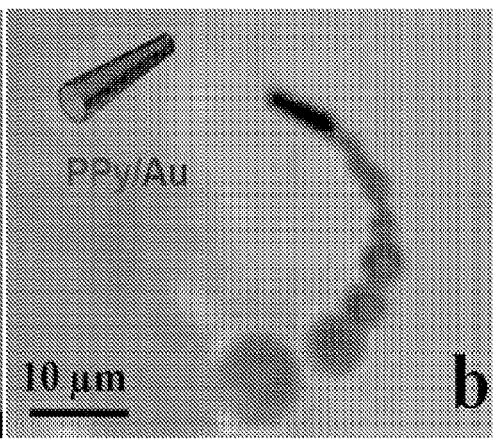
FIG. 26B

MEMBRANE TEMPLATE SYNTHESIS OF MICROTUBE ENGINES

CROSS REFERENCE TO RELATED APPLICATIONS

This document is a 35 USC §371 National Stage application of International Application No. PCT/US2012/000269 filed Jun. 4, 2012, which claims the priority of U.S. provisional application No. 61/492,782 entitled "MEMBRANE TEMPLATE SYNTHESIS OF CATALYTIC MICROTUBE ENGINES" filed on Jun. 2, 2011, the disclosures of which are incorporated by reference as part of this document.

STATEMENT REGARDING FEDERALLY SPONSORED RESEARCH OR DEVELOPMENT

This invention was made with government support under grant CBET 0853375 awarded by the National Science Foundation. The government has certain rights in the invention.

TECHNICAL FIELD

This patent document relates to systems, devices, and processes with respect to nano or microstructures and machines based on such structures.

BACKGROUND

Nanotechnology provides techniques or processes for fabricating structures, devices, and systems with features at a molecular or atomic scale, e.g., structures in a range of one to hundreds of nanometers in some applications. For example, nano-scale devices can be configured to sizes similar to some large molecules, e.g., biomolecules such as enzymes. Nano-sized materials used to create a nanostructure, nanodevice, or a nanosystem that can exhibit various unique properties that are not present in the same materials scaled at larger dimensions and such unique properties can be exploited for a wide range of applications.

SUMMARY

Techniques, systems, and devices are disclosed for fabricating and implementing self-propelling nanostructures and microstructures using membrane template electrodeposition.

In one aspect, a method is provided for fabricating one or more microtubes to include depositing a first layer on a template that has one or more holes to form a tube of the first layer in each hole; depositing a second layer over the first layer inside each hole of the template to form a bilayer microtube formed of the first and second layers inside each hole; and separating the template from each bilayer microtube.

In another aspect, a method is provided for fabricating one or more microtube to include depositing a first layer on a template that has one or more holes to form a tube of the first layer in each hole; depositing an intermediate second layer over the first layer inside each hole; depositing a third layer over the intermediate second layer inside each hold to form a trilayer microtube formed of the first, intermediate second, and third layers inside each hole; and separating the template from each trilayer microtube.

The subject matter described in this patent document can be implemented in specific ways that provide one or more of the following features. For example, the disclosed technology includes techniques to fabricate self-propelled chemically-powered catalytic nano/micromotors that can propel by bubble-induced propulsion in a fuel fluid including biological fluids and salt-rich environments. For example, the exemplary membrane template electrodeposition techniques can be implemented to mass produce conical shape microtubes (e.g., with yields of millions of microtubes in ~30 min). In addition, for example, fabrication of trilayer microtubes (e.g., with polymer, magnetic and catalytic layers) by means of the disclosed subject matter can provide multifunctional microtubes, which can facilitate motion control in various applications. For example, using the disclosed methods, microtubes of both polymer and metal layers can be fabricated at a high yield with scalable size in both diameter and length. For example, the speed of exemplary catalytic microengines produced using the exemplary technique can be increased in hydrogen peroxide and can be faster than microengines produced by other techniques. The exemplary catalytic microengines produced using the disclosed techniques can also move rapidly in a very low hydrogen peroxide level (e.g., down to 0.2% concentration). The exemplary microtubes exhibit excellent propulsion characteristics in diverse biological fluids and can be used in diverse biomedical applications, e.g., lab-on-chip diagnostics, cell sorting, target isolation, targeted drug delivery, and microsurgery. For example, in some implementations, the nano/micromotors of the disclosed technology can be engineered as immuno-nano/microscale machines that can isolate cells and/or target molecules from complex samples in vitro in a variety of biomedical applications, e.g., including drug delivery to biosensing. Also, for example, the described chemically-powered nanomotors and micromotors can be configured to move and pick-up/transport payloads in physiological conditions, e.g., within environments having high ionic strength, such as biological fluids.

BRIEF DESCRIPTION OF THE DRAWINGS

FIGS. 25A and 25B show images of the propulsion of exemplary PPy-based tubular microengine using silver and a platinum-nickel alloy inner layer.

FIG. 26A shows an SEM image of an exemplary PPy/Au$_{rough}$ bilayer microtube engine.

FIG. 26B shows an image of the biocatalytic propulsion of an exemplary PPy/Au-catalase microtube engine in a fuel fluid.

Like reference symbols and designations in the various drawings indicate like elements.

DETAILED DESCRIPTION

Figure 1A:
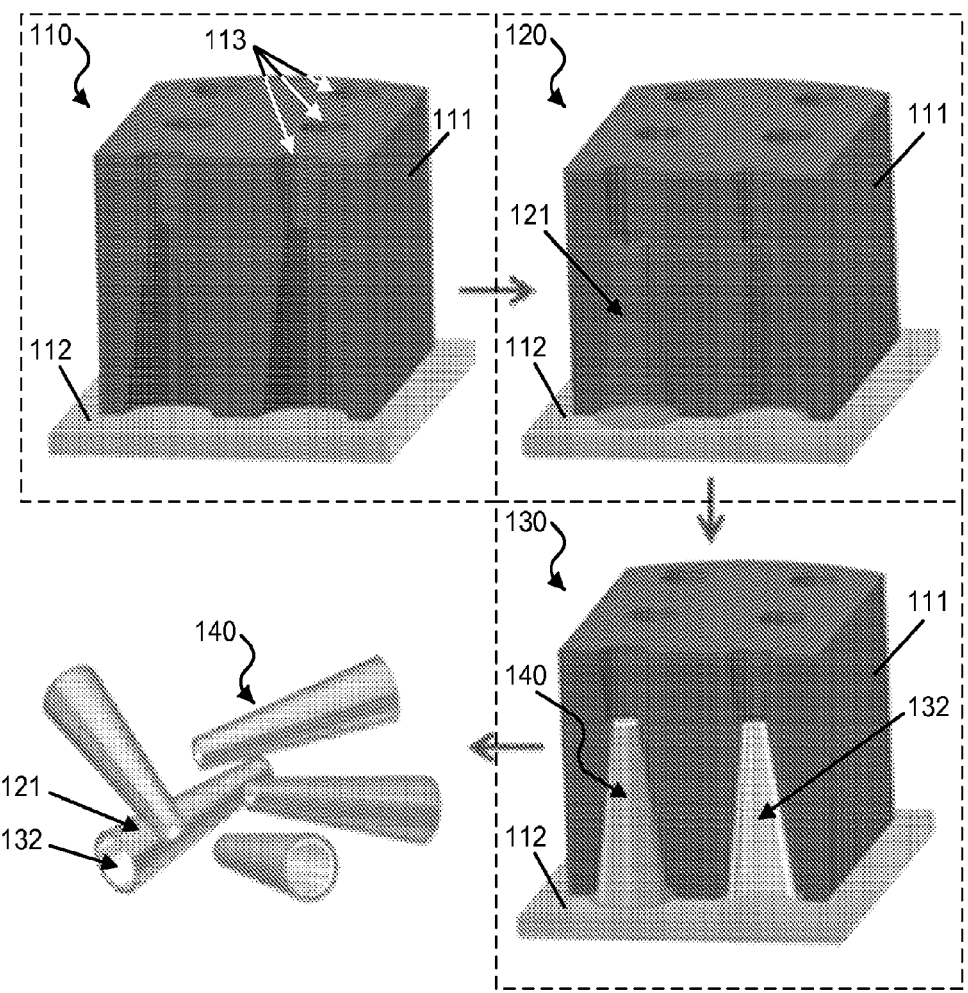
FIG. 1A shows a schematic diagram of an exemplary membrane-template electrodeposition fabrication process of microtube engines.

The techniques, systems, and devices described in this patent document can be used for production of nanoscale or microscale structures using the disclosed techniques including membrane template electrodeposition that are capable of autonomous movement and additional functionalities, e.g., including pick-up and transport of targeted payloads. For example, the engineered microstructures of the present technology can be configured as microtube rockets or microrockets, microtube engines or microengines, microtube motors or micromotors, micromachines, microtubes, and microcones.

In one aspect, the disclosed technology includes synthetic chemically-powered nanoscale motors that can self-propel in a fluid environment by converting energy into movement and forces. Among these exemplary chemically-powered nanomotors, catalytic microtube engines of the disclosed technology can exhibit efficient bubble-induced propulsion in relevant biological fluids and salt-rich environments containing a fuel substance. For example, these exemplary catalytic microtube engines can propel in a fluid by a gas-bubble propulsion mechanism based on the fuel fluid and the shape/geometry and inner surface material of the microengine structure. An exemplary catalytic microtube engine can be structured to include a large opening and a small opening that are on opposite ends of the microtube, in which the microtube includes a tube body connecting the openings and has a cross section spatially reducing in size along a longitudinal direction from the large opening to the small opening. The microtube engine can include a layered wall which includes an inner layer having a catalyst material that is reactive with a fuel fluid to produce bubbles exiting the tube from the first large opening to propel the tube to move in the fuel fluid. Additionally, the layered wall of the microtube engine can include an external layer formed of a material capable of being functionalized, e.g., by a molecular layer functionalized onto the external layer of the tube and structured to attach to a target molecule. For example, the inner layer can include a surface exposed to the fuel fluid that includes a catalyst material, e.g., platinum (Pt).

In some implementations, a microengine based on the disclosed technology can autonomously move by facilitating the entrance of a fuel (e.g., hydrogen peroxide ($H_2O_2$)) through the small radial opening of the microengine. Catalytically-generated gas bubbles (e.g., oxygen microbubbles ($O_2$)) can be formed and travel along the sloped transition of the inner surface of the microengine. The oxygen microbubbles can be ejected out from the large radial opening of the microengine, which generates a force propelling the microengine in the fluid. For example, the fluid can be a biological sample, e.g., including biological fluids, such as, but not limited to, aqueous humour and vitreous humour, bile, blood (e.g., blood serum, blood plasma), cerebrospinal fluid, intracellular fluid (e.g., cytoplasm) and extracellular fluid (including interstitial fluid, transcellular fluid, plasma), digestive fluid (including gastric juice and intestinal juice), lymphatic fluid and endolymph and perilymph, mucus (including nasal drainage and phlegm), peritoneal fluid, pleural fluid, saliva, sebum (e.g., skin oil), semen, sweat, tears, urine, vaginal fluids, and bacterial lysates. Other exemplary fluids can include non-biological fluids, such as (but not limited to), for example, pure water, salt-containing water, sugar-containing water, juice, and oil-based fluids.

Such a microengine can be configured to include additional functionalities. For example, such a microengine can be functionalized to capture and transport substances and organisms, e.g., such as biomolecules or living cells (e.g., among multitudes of other cells, e.g., normal cells). For example, upon encountering target cells in the biological fluid, the functionalized surface containing ligand molecules can recognize integrins or other biomolecules to which the ligand molecules have an affinity on the surface of the target cells. Based on recognition of the surface integrins of the target cell by the ligand molecules functionalized to the microengine, such a microengine can be designed to allow selective pick-up and transport of the cancer cell by the functionalized microengine over a preselected path. For example, chemically functionalized microengines can be designed to continue to exhibit efficient locomotion and a large towing force. For example, target biomolecules can include nucleic acids, lipids, carbohydrates, peptides, proteins, enzymes, hormones, antibodies, glycoproteins, glycolipids, organelles, endotoxins, viruses, and other biological materials and biomarkers. Exemplary living organisms can include cells, e.g., healthy cells, cancer cells, bacterial cells, and other types of cells.

Components or structures of microengines can be prepared by using various techniques, including, e.g., top-down photolithography, e-beam evaporation, and stress-assisted rolling of functional nanomembranes on polymers into exemplary microtube engines. Some implementations of these fabrication processes can create complexities in their practical utility and can lead to expensive costs (e.g., clean-room costs). The present technology provides techniques for preparing the disclosed microengines using a membrane-template mass production approach that simplifies the fabrication of micromachines. For example, an exemplary membrane-template electrodeposition technique can include using microporous membranes containing a large number of uniform conical pores (e.g., including a double conical pore array) to deposit polymeric and metallic materials to form the microtubes. The exemplary membrane-template electrodeposition method can be implemented to synthesize the disclosed microtube engines in a manner that is inexpensive to produce high yields.

FIG. 1A shows a schematic diagram of an exemplary membrane-template electrodeposition process for preparation of microtube engines of the disclosed technology. This exemplary process uses a membrane-template mass production to produce bilayer microtube engines including a polyaniline (PANT) outer layer and platinum inner layer using porous membranes. The exemplary process 110 is shown to assemble a porous membrane 111 having conical pores 113 to a substrate 112. The conical pores 113 includes an internal tubular section that has a cross section that spatially reduces in size along a longitudinal direction from the large opening to the small opening. In the example in FIG. 1A, each conical pore 113 includes two tubular sections where they share the common small opening so that the cross section of each conical pore 113 begins with the first large opening from the top surface of the template to gradually reduce in size to a smallest cross section and then gradually increase in size to the second large opening on the bottom surface of the template. In this design, each conical pore 113 includes two conical sections that shore the same small opening. The two conical sections may be structured to form an asymmetrical double cone pore structure with respect to the smallest section shared by the two conical sections. In the examples provided below, only one conical section of the asymmetrical double cone pore structure is used for forming the bilayer microtube engines.

Various processes can be used to form the layers for bilayer microtube engines inside the conical pores 113. For example, the process 110 can include a layer of a conductive material onto one porous side of the membrane 111 to form the substrate 112 via a suitable process, e.g., a sputtering process, an electron-beam evaporation process, an atomic layer deposition (ALD) process, or a chemical vapor deposition (CVD) process. For example, the membrane 111 can include a large number of pores on a single membrane material, e.g., the common polycarbonate membranes have a pore density of $10^5$-$6\times10^8$ pores/cm$^2$, which can enable the mass production of the microtube structures. The membrane 111 can include different pore size (e.g. 0.6 µm, 1 µm, 2 µm, 5 µm). In some examples, the membrane 111 can include a cyclopore polycarbonate membrane with a 20 µm thickness having an asymmetrical double cone pore structure with a 2 µm diameter at both openings and a 1 µm diameter as a minimum diameter internally within the pores. The substrate 112 can include an electrically conductive material, e.g., such as gold, silver, copper, aluminum or others. The assembled porous membrane-substrate can be used as a working electrode.

In FIG. 1A, the exemplary membrane template electrodeposition process can include a process 120 to deposit an outer layer 121 (e.g., of a polymer material, including polyaniline) to form single-layer structure within the pores 113 of the membrane 111. For example, aniline can be electropolymerized into the pores 113 of the membrane 111, in which polyaniline can grow as a tube structure, e.g., due to coupling of oxidized monomers that bind to the negatively charge wall of the membrane 111. For example, aniline monomers can polymerize on the inner wall of the membranes due to solvophobic effects and electrostatic effects, leading to a rapid formation of a polyaniline film.

Still referring to FIG. 1A, the exemplary membrane-template electrodeposition process can include a process 130 to deposit an inner layer 132 (e.g., a catalytic material including Pt) to form bilayer microtubes 140 within the pores 113 of the membrane 111. For example, a platinum layer can be subsequently plated along the inner surface of the polymer layer 121 (e.g., the PANI layer) using a galvanostatic method. For example, the high conductivity property of aniline in acid condition can provide support for platinum deposition, leading to a formation of the bilayer tube structure of platinum inside the PANI layer within membrane pores. Subsequently, the exemplary membrane-template electrodeposition process can include a process to dissolve the membrane 111 and release of the bilayer microtubes 140. For example, dissolution of the membrane 111 can include the use of methylene chloride, among other organic solvents. The resulting conical bilayer microtube structure 140 can be preserved after the template dissolution.

In some implementations, the exemplary membrane-template electrodeposition process can include additional deposition processing to deposit one or more intermediate layers between the outer layer 121 and inner layer 132. For example, the additional deposition processing can be implemented subsequent to the process 120 and prior to the process 130 to form a trilayer structure or other multilayer structures within the pores 113 of the membrane 111. In some examples, a magnetic material layer (e.g., nickel) can be subsequently plated along the inner surface of the polymer layer 121 (e.g., the PANI layer) using a galvanostatic method. For example, by depositing an intermediate magnetic material, the steering of the exemplary trilayer or multilayer microtube can be controlled via magnetic steering/motion control, e.g., by an external magnetic field.

Figure 1B:
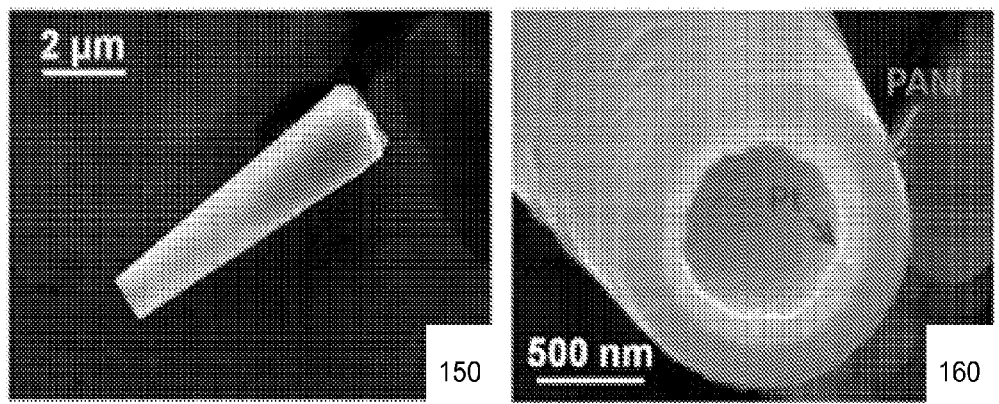
FIG. 1B shows scanning electron microscopy (SEM) images of exemplary PANI/Pt bilayer microtube engines.

FIG. 1B shows scanning electron microscopy (SEM) images 150 and 160 of the exemplary PANI/Pt bilayer microtube engines. The image 150 shows a side view of a bilayer PANI/Pt microstructure, and the image 160 shows a cross-view of the bilayer PANI/Pt microstructure. For example, the exemplary structure shown in FIG. 1B is an 8-µm long conical microtube with a defined geometry including a larger outer diameter of 2 µm and a smaller outer diameter of 1.1 µm, and a larger inner opening diameter of 1.5 µm and a smaller inner opening diameter of 0.5 µm, with a taper angle of 3.2° between the smaller and larger openings. The exemplary PANI and Pt layers, shown in the cross-view image 160, include a thickness of 180 nm and 80 nm, respectively. The exemplary microtube engines can be fabricated with significantly larger openings, lengths, and layer thicknesses using the disclosed membrane-template synthesis techniques (e.g., including openings in a 5-10 μm diameter range).

Exemplary fabrication processes and implementations were performed to demonstrate the uniform and efficient production and the functionalities and capabilities of the disclosed microengine technology. For example, multilayer catalytic microtubes were prepared using the described membrane template-directed electrodeposition process.

In one example, a cyclopore polycarbonate membrane, e.g., containing 2 μm diameter conical-shaped micropores, was employed as the exemplary template. A 150 nm gold film was sputtered on one side of the porous membrane to serve as working electrode. A Pt wire and an Ag/AgCl with 3 M KCl were used as counter and reference electrodes, respectively. The exemplary membrane was then assembled in a plating cell with an aluminum foil serving as contact. For example, polyaniline was distilled before use at a vapor temperature of 100° C. and a pressure of 13 mmHg, e.g., in which the distilled aniline solution was used within 3 days. For fabrication of exemplary PANI/Pt bilayer microtube engines, polyaniline microtubes were electropolymerized for 5 sec at +0.80 V from a plating solution containing 0.1 M $H_2SO_4$, 0.5 M $Na_2SO_4$ and 0.1 M aniline. Subsequently, the inner Pt tube was deposited galvanostatically at −2 mA for 3600 sec from a platinum plating solution. For fabrication of exemplary PANI/Ni/Pt trilayer microtube engines, polyaniline microtubes were deposited from a plating solution containing 0.1 M $H_2SO_4$, 0.5 M $Na_2SO_4$ and 0.1 M aniline and electropolymerized at +0.8 V for 5 sec; then a nickel layer was deposited from a nickel plating solution containing 20 g/L $NiCl_2.6H_2O$, 515 g/L $Ni(H_2NSO_3)_2.4H_2O$, and 20 g/L $H_3BO_3$ at −1.0 V (vs. Ag/AgCl) for 1 C; finally, the inner Pt tube was deposited galvanostatically at −2 mA for 1800 sec. For either configurations of the multilayer microtube engines, the sputtered gold layer substrate was completely removed, e.g., by hand polishing with 3-4 μm alumina slurry (e.g., which can be indicated by visual inspection of the membrane color). For example, an incomplete removal of the substrate can result in bubbles emerging from the smaller opening (yet without compromising the performance). The membrane was then dissolved in methylene chloride for 10 min to completely release the microtubes. The microtubes were collected by centrifugation at 6000 rpm for 3 min and washed repeatedly with methylene chloride (e.g., three times), followed by ethanol and ultrapure water (e.g., 18.2 MΩcm), twice of each, with a 3 min centrifugation following each wash. The exemplary collected microengines were stored in nanopure water at room temperature when not in use.

The exemplary microengine fabrication method can be characterized with good reproducibility. For example, two batches tested from different membranes yielded average speeds of 286 and 281 μm/s, with relative standard deviations of 16.4 and 18.2%, respectively. The total number of microengines per batch was approximately 30. The exemplary fluid that the fabricated microengines propelled within contained 1.0% $H_2O_2$ and 1.6% sodium cholate. The exemplary microengines propelled continuously for over 20 min in 15 μL mixed solution (e.g., until this exemplary sample solution dried up).

The exemplary template electrochemical deposition technique to fabricate microtube engines was carried out with a CHI 621A potentiostat (CH Instruments, Austin, Tex.). Scanning electron microscopy (SEM) images were obtained with a Phillips XL30 ESEM instrument, e.g., using an acceleration potential of 20 kV. Mapping analysis was investigated by Oxford EDX attached to SEM instrument and operated by Inca software. An inverted optical microscope (Nikon Instrument Inc. Ti-S/L100), coupled with a 40× objective, a Photometrics QuantEM 512/SC camera (Roper Scientific, Duluth, Ga.) and a MetaMorph 7.6 software (Molecular Devices, Sunnyvale, Calif.) were used for capturing movies, e.g., at a frame rate of 30 frames per sec. The speed of the microengines was tracked using a MetaMorph tracking module and the results were statistically analyzed using Origin software.

For example, in order to self-propel catalytic microengines, aqueous hydrogen peroxide solutions with concentrations ranging from 0.2-5.0% were used as chemical fuels, e.g., containing 0.33-5.0% (w/v) sodium cholate to reduce the surface tension and facilitate the engine propulsion. For example, below 0.5% peroxide, the fraction of moving microengines decreased due to the lower bubble frequency (e.g., weaker bubbling thrust). For example, in addition to the exemplary implementations of the fabricated microengines in fluids containing aqueous hydrogen peroxide and sodium cholate solutions, exemplary implementations of the fabricated microengines were performed in human serum samples from human male AB plasma and cell culture media. For example, these exemplary human serum implementations were carried out by mixing sequentially 5 μL microengine solution, 5 μL 10% sodium cholate, 10 μL biological media and 5 μL 7.5% $H_2O_2$, e.g., a final solution corresponding to 40% of the raw samples.

Figure 2A:
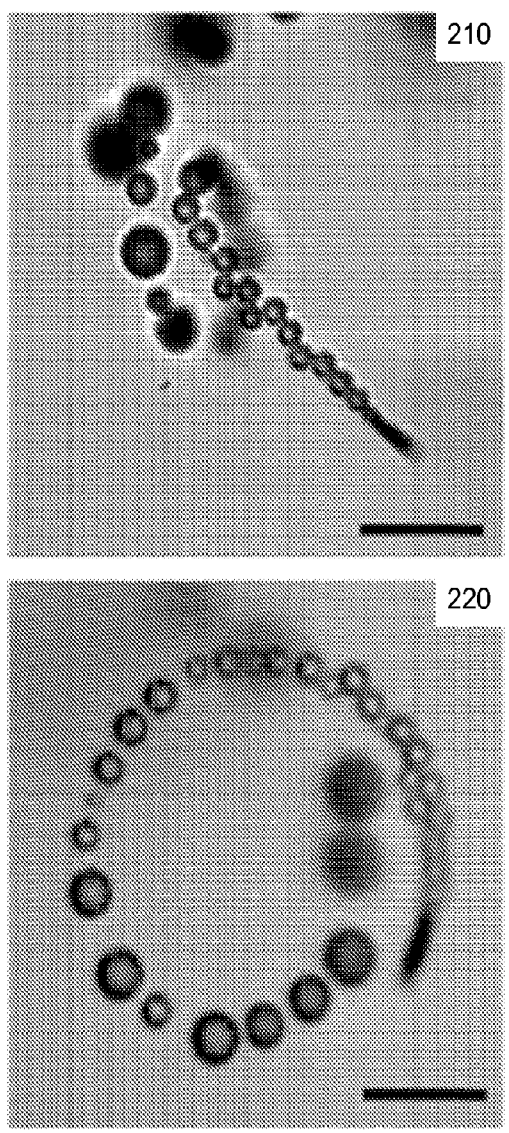
FIGS. 2A and 2B show images of trajectories and motion of exemplary tubular catalytic PANI/Pt microengines.

FIG. 2A shows images 210 and 220 of exemplary tubular catalytic PANI/Pt microengines demonstrating trajectories including spiral motion (e.g., shown in the image 210) and circular motion (e.g., shown in the image 220) during a 3 sec period. The trajectories are visualized by microbubble tails in a fluid including a 1% $H_2O_2$ solution with a sodium cholate level of 0.33% (w/v). The exemplary images 210 and 220 demonstrate the substantially large propulsion power of the template-prepared PANI/Pt microtube engines. The two microengines move rapidly in spiral and circular trajectories, with an average speed of 120 μm/s. For example, as shown in FIG. 2A, long oxygen bubble tails were released from the wider tubular openings, e.g., with individual microbubbles size of ~2.5 μm. The exemplary scale bars shown in FIG. 2A represents 20 μm.

Figure 2B:
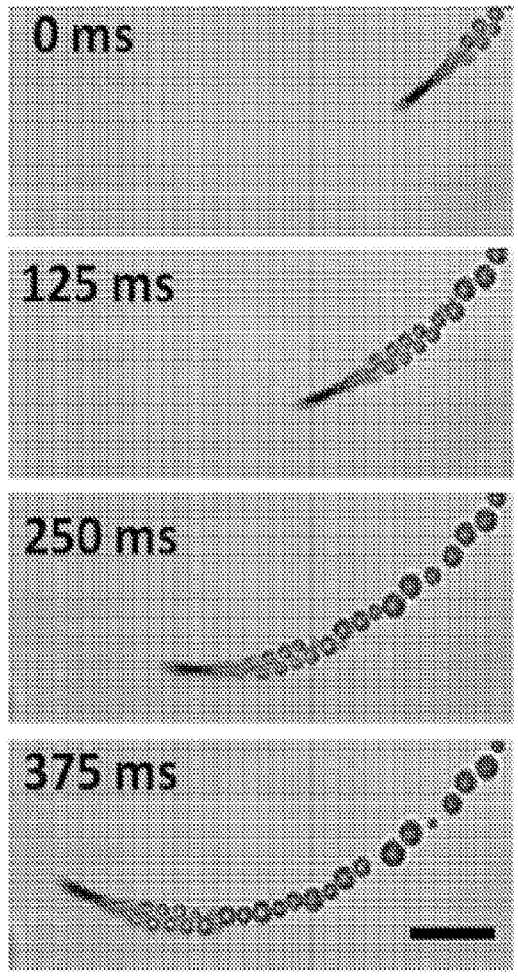

FIG. 2B shows time lapse images in 125 ms intervals demonstrating the motion of an exemplary PANI/Pt bilayer catalytic microengine in a fluid containing 1% hydrogen peroxide fuel (e.g., including 0.33% sodium cholate). The exemplary scale bar shown in FIG. 2B represents 20 μm.

Figure 3:
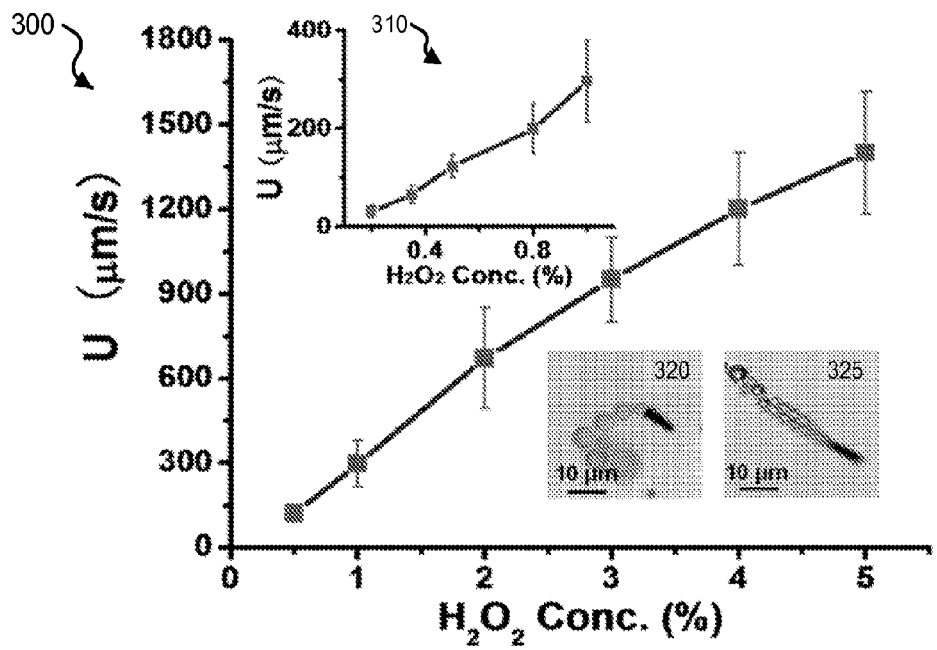
FIG. 3 shows a data plot demonstrating the dependence of an exemplary microengine's speed upon the hydrogen peroxide fuel concentration.

FIG. 3 shows a data plot 300 demonstrating the dependence of an exemplary PANI/Pt catalytic microengine's speed upon the hydrogen peroxide concentration over a 0.2 to 5.0% range, in the presence of 1.6% (w/v) sodium cholate (n=60). The data plot 300 includes an inset 310 showing the speed profile over the 0.2-1.0% peroxide range. FIG. 3 also shows inset images 320 and 325 demonstrating the propulsion in the presence of 0.3% hydrogen peroxide (e.g., shown in the image 320) and 0.5% hydrogen peroxide (e.g., shown in the image 320).

As shown in FIG. 3, the concentration of hydrogen peroxide fuel can strongly influences the velocity of the catalytic microengines. For example, the average speed of the exemplary PANI/Pt microtubular engines increased from 123±21.4 μm/s (e.g., 15 body lengths/s) in the 0.5% hydrogen peroxide fuel to 1410±172 μm/s (e.g., ~180 body lengths/s) in a 5% hydrogen peroxide fuel. For example, the substantially increased speed of the PANI/Pt microengines over the entire range of the hydrogen peroxide fuel (e.g., 0-5% $H_2O_2$) reflected the higher pressure experienced by the bubbles. However, for example, using a low peroxide level (e.g., below 5% $H_2O_2$), the exemplary template bilayer microengines displayed a much faster speed than microengines fabricated using other techniques, e.g., microengines produced by rolled-up processes. For example, the fastest observed speed of the microengines exceeded 3 mm/s (e.g., more than 375 body lengths/s) in connection to 10% $H_2O_2$ and 1.6% sodium cholate. Exemplary implementations also show that such microengines can move in very low peroxide levels, e.g., as shown in the inset data plot 310 of FIG. 3. The inset 310 demonstrates the dependence of the microengine speed upon the hydrogen peroxide concentration over the 0.2-1.0% range. For example, well defined propulsion can be observed over this exemplary range of low peroxide concentrations, e.g., with speeds ranging between 25 and 285 μm/s. For example, a typical microtube movement of ~25 μm/s (e.g., over 3 body lengths/s) in a 0.2% $H_2O_2$ solution. In contrast, for example, the lowest peroxide level for propelling catalytic rolled-up microengines may include a 1.5% $H_2O_2$ solution, in which the maximum propulsion speed exhibited was a low speed of 1 body length/s.

Also, for example, the radius and frequency of the generated oxygen bubbles can be influenced by the level of peroxide fuel. The exemplary inset images 320 and 325 in FIG. 3 illustrate the representative bubble size of microtubular engines. For example, the bubble frequency was shown to increase greatly (e.g., from 16 Hz to 60 Hz) upon raising the peroxide level from 0.3 to 0.5%, while the bubble size was shown to decrease from 2.6 μm to 2.0 μm, respectively. For example, the larger bubbles with a lower frequency were associated with a lower speed (e.g., 40 μm/s in 0.3% hydrogen peroxide, as compared to 120 μm/s in 0.5% peroxide). It was also observed in the exemplary implementations that the average moving steps were close to the bubble radius. For example, in 0.5% hydrogen peroxide, in which the bubble radius was shown to be ~2 μm with a frequency of ~60 Hz, the microengine speed was shown to be 122 μm/s, e.g., which nearly corresponds to the product of the bubble and frequency, indicating that the drag forces on the engines and bubbles are comparable.

Figures 4A, 4B:
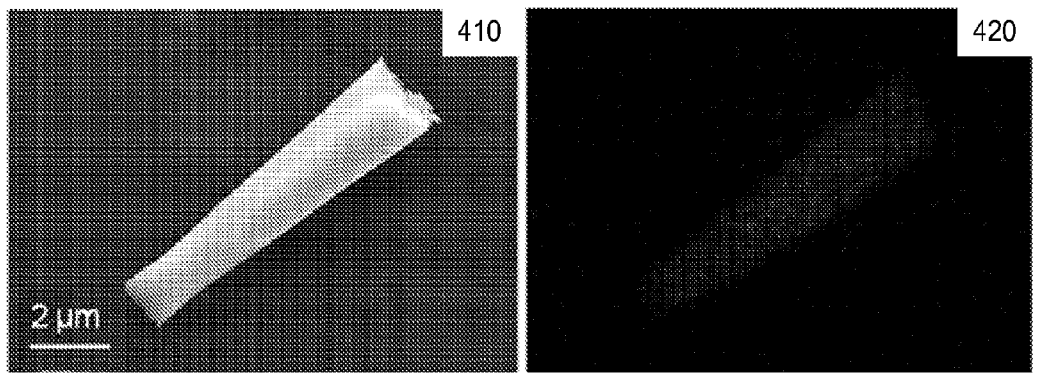
FIGS. 4A-4C show images of an energy-dispersive X-ray (EDX) mapping analysis of exemplary bilayer PANI/Pt microtubes.
Figure 4C:
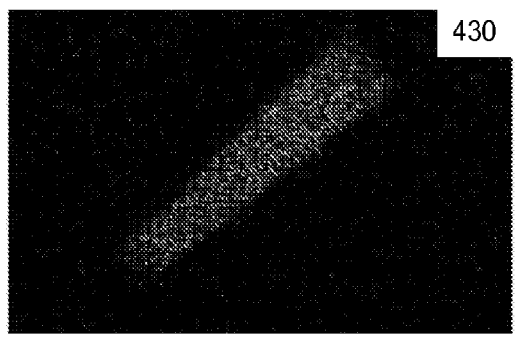

FIGS. 4A-4C show images of an energy-dispersive X-ray (EDX) mapping analysis of exemplary bilayer PANI/Pt microtubes. FIG. 4A shows a SEM image 410 of a bilayer microtube; FIG. 4B shows an image 420 of an EDX mapping result of the distribution of carbon; and FIG. 4C shows an image 430 of an EDX mapping result of the distribution of platinum. The presence of both platinum and carbon (from PANI) within the conical microtube shown in FIGS. 4B and 4C confirms the bilayer content.

Figure 5:
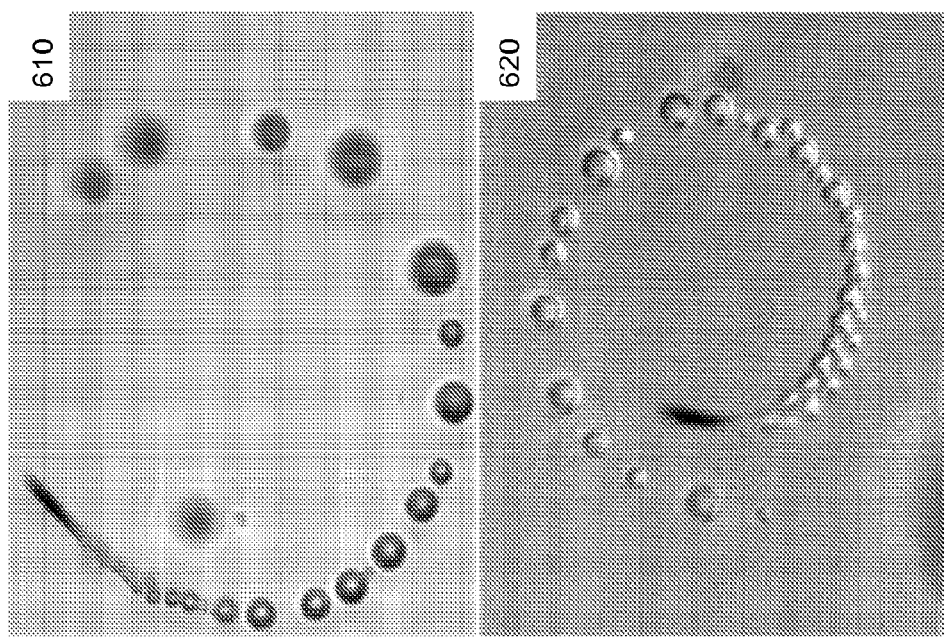
FIG. 5 shows a data plot demonstrating the influence of sodium cholate concentration in the fluid on the speed of the exemplary catalytic microengines.

The influence of the exemplary surfactant concentration (e.g., sodium cholate in these exemplary implementations) upon the speed of catalytic microengines was also examined. FIG. 5 shows a data plot 500 demonstrating the influence of sodium cholate concentration on the speed of the catalytic microengines in the presence of 1% and 2% hydrogen peroxide. For example, increased speed was observed upon raising the surfactant concentration over a 0-5% range. For example, using a 1% $H_2O_2$ solution containing 0.33% sodium cholate, the exemplary microengines exhibited an average speed of 120 μm/s. The speed of the exemplary microengines increased to around 300 μm/s in 1.6% sodium cholate, and to 520 μm/s in 5% sodium cholate. For example, in the presence of the 2% $H_2O_2$ solution (along with 5% sodium cholate), the exemplary microengines moved at 1.0 mm/s. These exemplary changes reflect lower surface tension and reduced bubble size at higher surfactant levels.

Conventional catalytic nanowire motors operate only in low ionic-strength aqueous solutions and hence cannot be applied to realistic biological environments. For example, the nano/microengines of the disclosed technology can address this ionic-strength limitation and can expand the scope of nanomotors to salt-rich environments. For example, FIG. 6 illustrates the movement of the template-prepared microengine in cell culture media and human serum, respectively.

Figure 6:
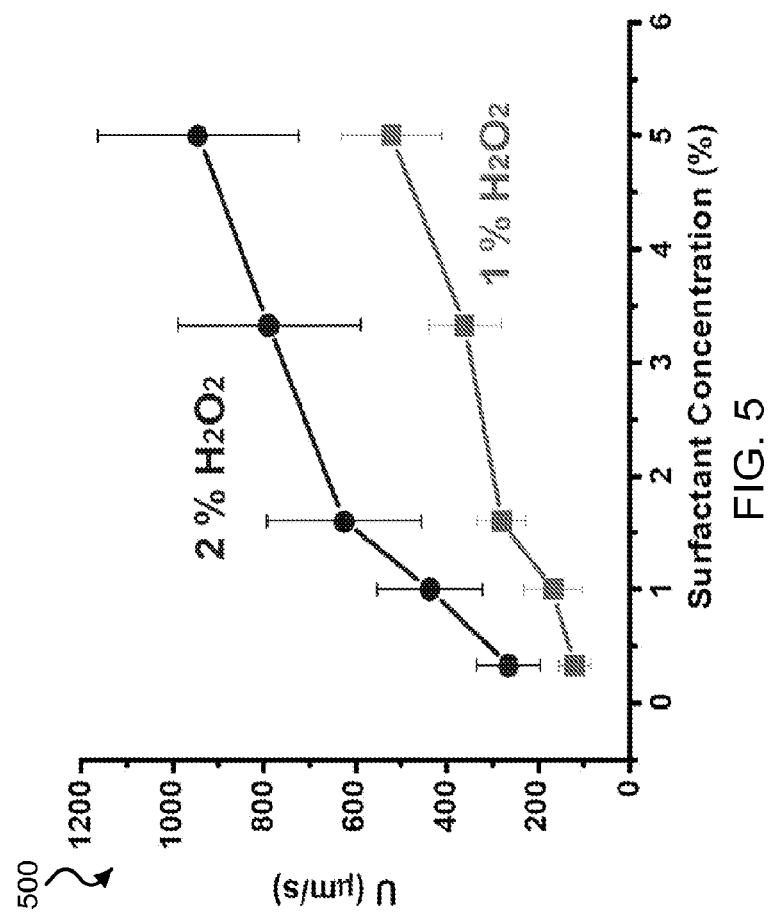
FIG. 6 shows images of the propulsion motion of exemplary catalytic bilayer microengines in biological media.

FIG. 6 shows an image 610 of the motion of an exemplary bilayer catalytic microengine in cell culture media with 1.5% $H_2O_2$, 2% sodium cholate. FIG. 6 also shows an image 620 of the motion of an exemplary bilayer catalytic microengine in human serum with 1.5% $H_2O_2$, 2% sodium cholate. For example, the exemplary microengines propelled efficiently in these biological media, e.g., with high average speeds of 150 μm/s in cell culture (as shown in the image 610) and 95 μm/s in serum (as shown in the image 610). For example, the decrease of speed, as compared to more than ~300 μm/s in water (under similar conditions), can be attributed to viscosity effects (e.g., ~1.5 mPa·s for human serum). Also, for example, a slower speed of ~200 μm/s was observed in a high ionic aqueous solution (e.g., 3 M NaCl, with a viscosity of ~1.2 mPa·s).

For example, if the microengine structures were configured as a cylinder microrod (e.g., such as a 8 μm in length and 2 μm diameter at both openings), moving at the speed of 1400 μm/s, an estimated drag force can be determined by using the Stokes' drag theory equation:

$$F_d = \frac{2\pi\mu LU}{\ln(L/a) - 1/2} \qquad (1)$$

where $F_d$ is the fluid resistance, U is the speed in the microengine, g is the fluid dynamic viscosity, and L and a are the length and radius of the microtube, respectively. The estimated drag force of this exemplary cylinder microrod microengine can be determined to be 45 pN, which would be sufficient for transporting large cargos such as cells. It is noted that the fluid may not freely flow through such a cylinder microrod microengine because of the oxygen bubbles in the fluid flow path.

The results of the exemplary implementations demonstrated that the disclosed membrane template electrodeposition fabrication techniques can mass produce microengines of a comparatively small size. For example, the disclosed methods can be used to synthesize microengines with varying diameters and lengths (e.g., including diameters in a range of 1-3 μm and lengths in a range of 4-20 μm). Additionally, the results of the exemplary implementations demonstrated that the exemplary catalytic microengines fabricated by the disclosed membrane template electrodeposition techniques can move at high speeds (e.g., >350 body lengths/s) and require very low fuel concentrations in a fluid (e.g., 0.2% hydrogen peroxide concentration). The results of the exemplary implementations demonstrated that the exemplary catalytic microengines can propel well in diverse biological fluids, and thus be utilized in diverse biomedical applications (e.g., lab-on-a-chip diagnostics, cell sorting, target isolation, microsurgery, and drug delivery, among other applications).

Figure 7:
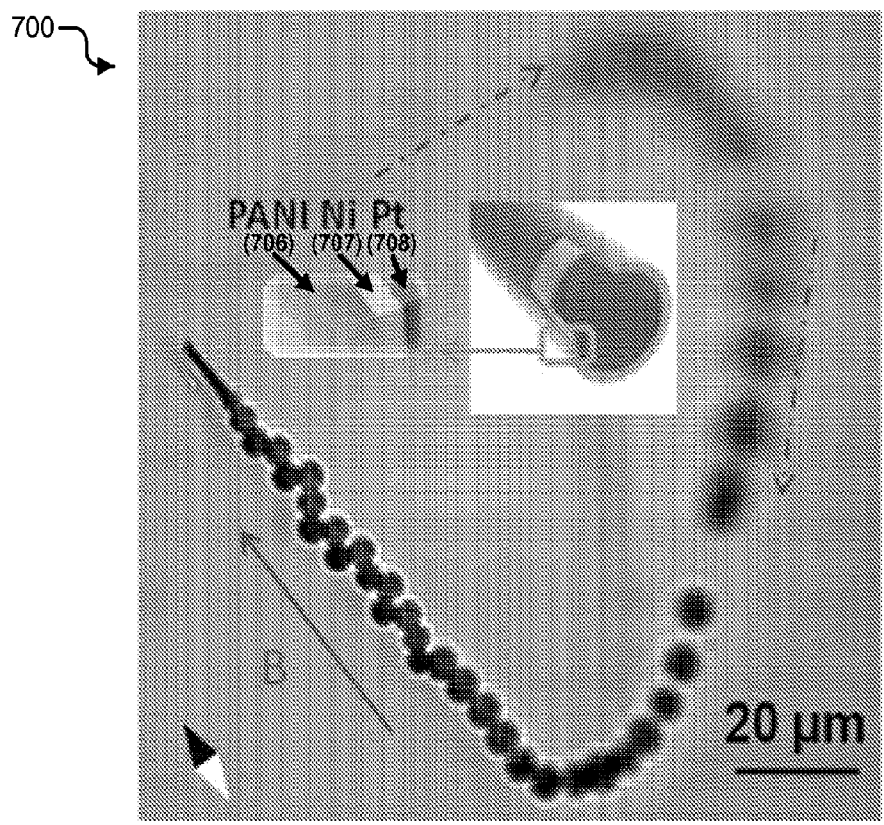
FIG. 7 shows an image demonstrating magnetic motion control of an exemplary catalytic PANI/Ni/Pt trilayer microengine.

Additional modifications to the structure (e.g., including the multilayer materials and/or geometry of structure) can be performed to configure the catalytic microengines for a variety of diverse applications. For example, the disclosed fabrication techniques can be employed to plate different outer or inner layer materials (e.g., polymers, metals, etc.) or additional intermediate layer(s) materials, e.g., which can be used to control the steering of the nano/microstructures. While the exemplary bilayer catalytic microengines (e.g., such as those shown in FIG. 2A) move randomly, it is also possible to guide them magnetically. For example, trilayer microengines can be produced using the exemplary process described and illustrated in FIG. 1A by depositing an intermediate ferromagnetic layer between the exemplary outer PANI layer 121 and the exemplary inner Pt layer 132 (e.g., such as a Ni layer, to form a trilayer PANI/Ni/Pt microengine). For example, by depositing an intermediate ferromagnetic (e.g., such as a Ni layer), the steering of an exemplary microengine can be controlled via magnetic means. FIG. 7 shows an image 700 demonstrating magnetic motion control of an exemplary PANI/Ni/Pt trilayer microengine. The image 700 includes an inset schematic showing the outer PANI layer 706, the intermediate nickel layer 707, and the internal platinum layer 708. The exemplary arrow in the image 700 represents the magnetic field (B) direction.

Figure 8:
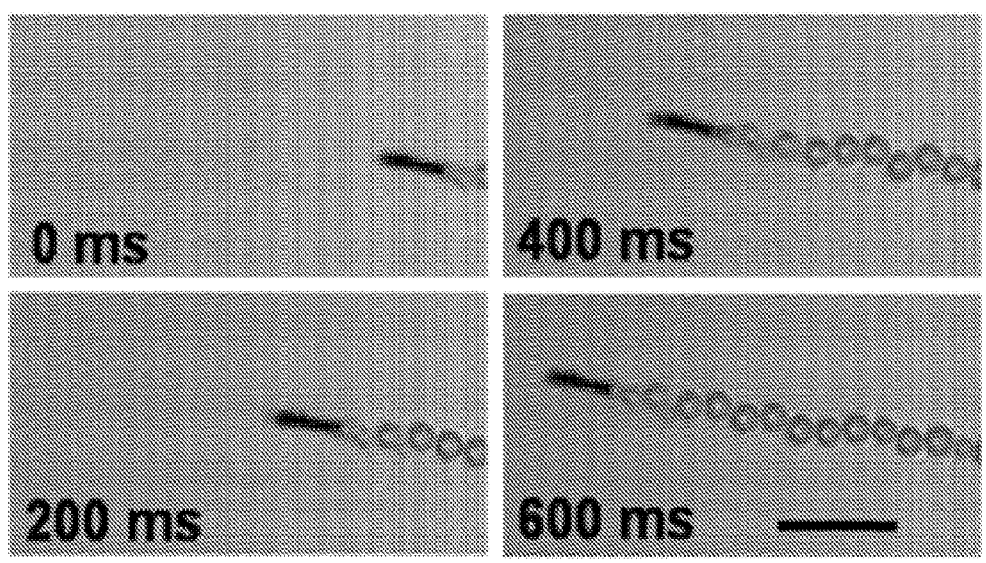
FIG. 8 shows time lapse images demonstrating the motion of an exemplary catalytic PANI/Ni/Pt trilayer microengine under a magnetic field.

FIG. 8 shows time lapse images in 200 ms intervals demonstrating the motion of an exemplary PANI/Ni/Pt trilayer catalytic microengine under the magnetic field in the presence of 1% $H_2O_2$ solution. A decrease in the speed of the exemplary trilayer microengine was demonstrated in this example, as compared to the exemplary bilayer microengines. For example, the magnetically-guided directional motion of the exemplary PANI/Ni/Pt microengine showed a decrease in speed to 80 µm/s, as compared to the 120 µm/s of the bilayer PANI/Pt microtubes (under the same conditions), e.g., reflecting the smaller opening diameter associated with the Ni layer. The exemplary scale bar shown in FIG. 8 represents 20 µm.

In another aspect, the disclosed technology can include exemplary nano/microtube structures can be configured to propel in a fluid by a gas-bubble propulsion mechanism based on the chemical reactions of inner surface material of the nano/microengine structure with acidic species in the fluid.

Exemplary zinc-based microtube engines (e.g., PANI/Zn bilayer microtubes) can be fabricated using the present membrane-template electrodeposition fabrication techniques to move by hydrogen-bubble propulsion in strongly acidic fluid environment. An exemplary acid-driven microtube engine can be structured to include a large opening and a small opening that are on opposite ends of the microtube, in which the microtube includes a tube body connecting the openings and has a cross section spatially reducing in size along a longitudinal direction from the large opening to the small opening. The microtube engine can include a layered wall in which an inner layer can include a chemically-reactive material (e.g., zinc (Zn)) exposed to the acidic fluid. For example, the PANI/Zn bilayer microtube engines can undergo effective autonomous motion in the acidic fluid environment without any additional chemical fuel. The propulsion in the acidic fluid can be driven by continuous thrust of hydrogen bubbles generated by the spontaneous redox reactions occurring at the inner layer surface (e.g., the inner Zn layer). For example, when the exemplary PANI/Zn bilayer microengines are immersed in a strongly acidic medium, a spontaneous redox reaction, e.g., involving the Zn oxidation along with generation of hydrogen bubbles, occurs on their inner Zn surface:

$$Zn\,(s) + 2H^+\,(aq) \rightarrow Zn^{2+}\,(aq) + H_2\,(g)\quad E^\circ = 0.76\,V \qquad (2)$$

leading to rapid propulsion that can exceed 100 body lengths/s. Zinc has a more negative redox potential than hydrogen and thus promotes hydrogen gas evolution. For example, Zn is a biocompatible 'green' nutrient trace element and thus represents an attractive material for the microengine inner layer. Other materials that can be employed as the inner layer material include metals, e.g., iron (Fe), aluminum (Al), cobalt (Co), tin (Sn), or lead (Pb). Such metals have a more negative redox potential than hydrogen and potentially can lead to similar hydrogen evolution like Zn.

Strongly acidic environments can be found everywhere in our life, from diverse industrial processes to our own human stomach. The autonomous movement of the disclosed microengines in such acidic media can thus be applied in diverse biomedical and industrial applications. For example, the exemplary acid-driven PANI/Zn microengines can also serve as an attractive platform for sensitive pH measurements in acidic environments.

Exemplary fabrication processes and implementations were performed to demonstrate the uniform and efficient production and the functionalities and capabilities of the disclosed microengine technology. For example, multilayer acid-driven microtubes were prepared using the described membrane template-directed electrodeposition process.

For example, PANI/Zn bilayer microtubes was fabricated within an exemplary cyclopore polycarbonate template e.g., containing 2 µm and 5 µm diameter conical-shaped micropores, which was employed as the exemplary template. A 75 nm gold film was sputtered on one side of the porous membrane to serve as working electrode. A Pt wire and an Ag/AgCl with 3 M KCl were used as counter and reference electrodes, respectively. The exemplary membrane was then assembled in a plating cell with an aluminum foil serving as contact. For example, polyaniline was distilled before use at a vapor temperature of 100° C. and a pressure of 13 mmHg, e.g., in which the distilled aniline solution was used within 3 days. For fabrication of exemplary PANI/Zn bilayer microtube engines, polyaniline microtubes were electropolymerized at +0.80 V for 0.02 C (and 0.1 C for the exemplary 5 µm pore sizes) from a plating solution containing 0.1 M $H_2SO_4$, 0.5 M $Na_2SO_4$ and 0.1 M aniline. Subsequently, a zinc layer has been deposited galvanostatically at −6 mA for 1800 sec (and 2400 sec for the exemplary 5 µm pore sizes) within the PANI layer using an 80 g L$^{-1}$ $ZnSO_4$/20 g L$^{-1}$ $H_3BO_3$ solution (buffered to pH=2.5 with sulfuric acid). For example, the sputtered gold layer substrate was completely removed, e.g., by hand polishing with 3-4 µm alumina slurry (e.g., which can be indicated by visual inspection of the membrane color). The membrane was then dissolved in methylene chloride or chloroform for 10 min to completely release the microtubes. The microtubes were collected by centrifugation at 6000 rpm for 3 min and washed repeatedly with methylene chloride or chloroform (e.g., three times), followed by ethanol and ultrapure water (e.g., 18.2 MΩcm), twice of each, with a 3 min centrifugation at 6000 rpm following each wash. The exemplary collected microengines were stored in nanopure water at room temperature when not in use. For example, to achieve the magnetic directional control of the microtube engines, the exemplary microtube solution was evaporated onto glass slides before the sequential E-beam deposition of 10 nm Ti (adhesion layer), 20 nm Ni (magnetic layer), over the microtubes. Implementations of the exemplary microtube engines were performed in human serum samples, e.g., from human male AB plasma (Sigma-Aldrich, St. Louis, Mo.), which were carried out by mixing sequentially 5 µL of the microtube solution with 5 μL 5% Triton X-100, 5 μL biological media and 5 μL 2 M HCl, leading to a final solution corresponding to 25% of the raw samples.

Figure 9A:
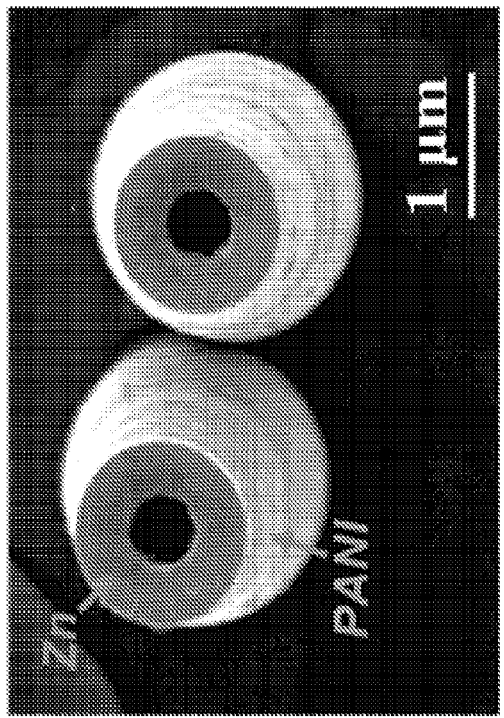
FIG. 9A shows a schematic illustration of an exemplary acid-driven PANI/Zn microengine in an acidic fluid environment.
Figure 9B:
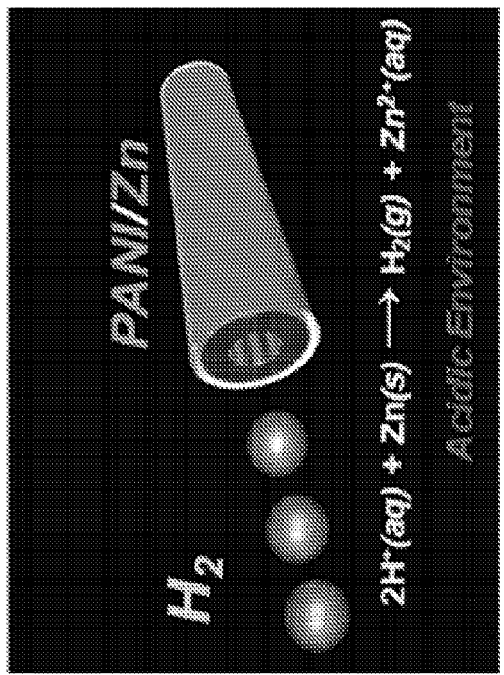
FIG. 9B shows an SEM image of exemplary PANI/Zn microtube engines.

FIG. 9A shows a schematic illustration of an acid-driven PANI/Zn microengine in an acidic fluid environment. FIG. 9B shows an SEM image of the top view of two PANI/Zn microtubes (e.g., prepared electrochemically using a membrane with 2 μm diameter pores). For example, the membrane template electrochemically produced microengines were configured to be ~10 μm long, having a front inner opening diameter of ~350 nm and a rear outer diameter of ~1.2 μm. These exemplary microtube engines included a ~150 nm thick PANI outer layer and a ~300 nm Zn inner layer. For example, the presence of carbon and zinc in the resulting bilayer microtubes was confirmed by EDX mapping analysis.

Figure 10:
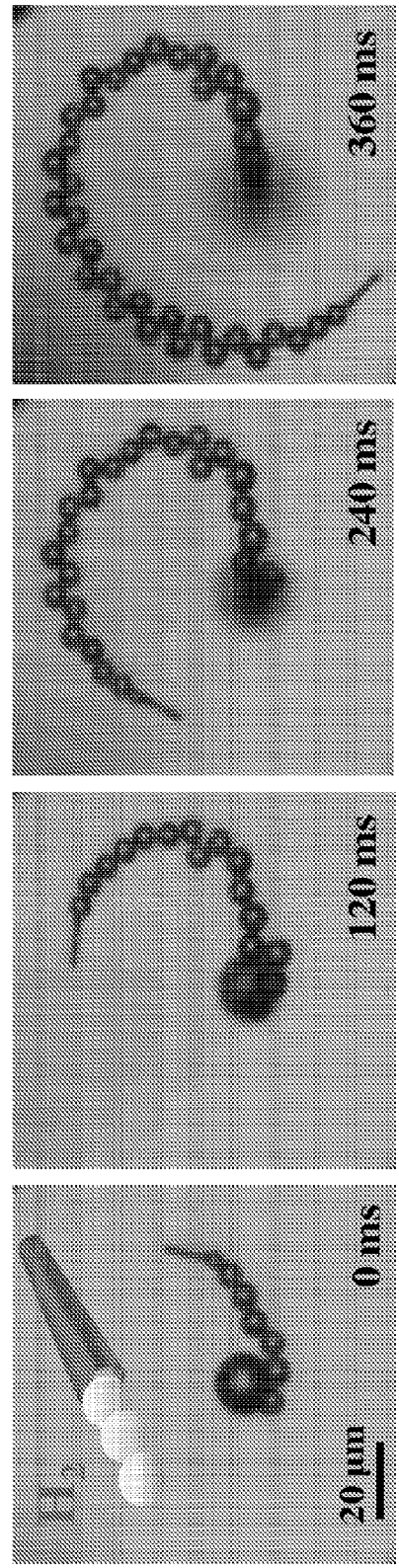
FIG. 10 shows time lapse images demonstrating the motion of an exemplary acid-powered PANI/Zn bilayer microengine.

FIG. 10 shows time lapse images in 120 ms intervals over a 360 ms period demonstrating the propulsion of an exemplary acid-powered PANI/Zn bilayer microengine (e.g., having 2 μm diameter at the larger opening) at 0, 120, 240, 360 ms, respectively. For example, the fluid medium included a 1 M HCl solution at pH=0 containing 1.67% Triton X-100. These images shown in FIG. 10 illustrate a tail of hydrogen microbubbles (e.g., ~4-5 μm in diameter) generated on the Zn surface of the inner layer and released from the rear of the exemplary microengine at a rate of 75 bubbles/sec. The exemplary microengine is self-propelled in the acidic fluid at a speed over 500 μm/s, which corresponds to a relative speed of nearly 50 body lengths/s.

Figure 11:
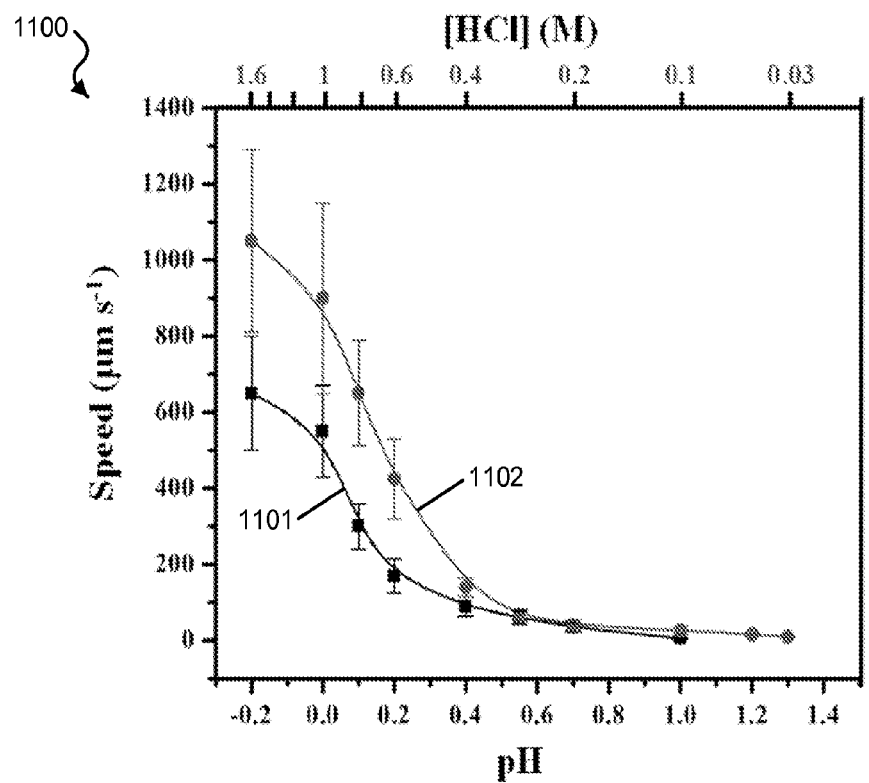
FIG. 11 shows a data plot showing the pH dependence of the speed of exemplary PANI/Zn microengines in solutions of different acidic concentrations.

For example, the speed of the acid-driven PANI/Zn microengine was shown to be dependent on the acid concentration. FIG. 11 illustrates the influence of the pH and HCl concentration upon the speed of the exemplary microengines. FIG. 11 shows a data plot 1100 that exhibits the pH dependence of the speed of exemplary PANI/Zn microengines in solutions of different HCl concentrations (e.g., over a range of 0-1.6 M). A 1.67% concentration of Triton X-100 was added as a surfactant in the fluid solution. The data plot 1100 includes a data curve 1101 of the exemplary microengines with a 2 μm larger opening of the tube structure and a data curve 1102 of the exemplary microengines with a 5 μm larger opening of the tube structure. Exemplary error bars show the standard deviations of the measured speeds.

For example, both exemplary microengines displayed their highest speed within the highest acid concentration examined (e.g., 1.6 M HCl, corresponding to pH −0.2). For the exemplary 2 μm microengine shown in the data curve 1101, the speed decreased gradually from 650 μm/s (at pH −0.2) to 550 μm/s (at pH 0.0), then more rapidly to 300 μm/s (at pH 0.2), and then slowly to 8 μm/s (at pH 1.0). The exemplary 5 μm microengine shown in the data curve 1102 displayed a similar trend, along with a higher initial speed, and slightly wider pH range. For example, the exemplary 5 μm microengine achieved a speed of 1050 μm/s (~100 body lengths/s) at pH −0.2, that decays gradually to 140 μm/s at pH 0.4 and then more slowly to 10 μm/s at pH 1.3. For example, the wider operational pH range can be associated with biomedical applications of the disclosed acid-driven microengines, e.g., such as movement in the extreme stomach environment of pH 0.8-2.0. The lifetime of the PANI/Zn acid-driven microengines can be influenced by the rate of the Zn dissolution, e.g., which may range from 10 sec to 2 min for these exemplary configurations. For example, this can be associated with the surrounding pH (that influences the rate of the Zn dissolution) and the amount of Zn present. For example, a prolonged movement of the exemplary 5 μm microengine over 1 min in a 60 mM HCl solution (pH=1.2) at a speed of 20 μm/s was observed.

The exemplary speed-pH profiles of FIG. 11 can form the basis for sensitive motion-based pH measurements in extremely acidic environments, e.g., where common glass pH electrodes lead to a large acid error. Microengine-based pH sensing could involve measurements of the speed and/or distance traveled by the microengine, e.g., which can be analogous to a motion-based DNA sensing techniques. Exemplary motion-based pH sensing may be implemented in applications including detecting changes in the stomach acidity and remote monitoring of etching baths in semiconductor processing. For example, changing movement in an acid gradient (e.g., chemotaxis) can also be sensed by implementing the exemplary acid-driven microengines.

Table 1 shows a comparison of the speed of the exemplary PANI/Zn microengines in the presence of different acids. For example, 0.5 M HCl, 0.25 M $H_2SO_4$ and 0.167 M $H_3PO_4$ were utilized along with 1.67% Triton X-100 surfactant.

TABLE 1

| Acid Type | Speed (μm/s) |
|---|---|
| HCl | 140 |
| $H_2SO_4$ | 80 |
| $H_3PO_4$ | 20 |

For example, while a speed of 140 μm/s was observed in 0.5 M HCl, significantly slower speeds of 80 and 20 μm/s were observed in $H_2SO_4$ and $H_3PO_4$, respectively, reflecting their decreasing acid dissociation constants. For example, such speed variations are consistent with the pH dependence of the PANI/Zn microengine observed in FIG. 11. In contrast, for example, no efficient propulsion was observed in a 0.5 M $HNO_3$ solution, although the zinc layer was dissolved. The lack of movement in nitric acid may reflect the generation of $N_2O$ (instead of $H_2$), which is much more soluble in water, according to:

$$4Zn+10HNO_3(\text{dilute}) \rightarrow 4Zn(NO_3)_2+N_2O+5H_2O \quad (3)$$

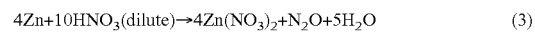

A magnetic layer can be incorporated into the acid-driven multilayer microengines, e.g., such as the PANI/Pt microengines. For example, the described membrane template electrodeposition fabrication techniques can further include implementing E-beam deposition of Ti and Ni layers on the outer PANI surface of the exemplary PANI/Pt microengines. For example, the addition of the magnetic material layers can allow magnetic control of their directionality and cargo pick up.

Exemplary implementations of the Ni/Ti/PANI/Zn microengines (e.g., having a 5 μm diameter at the larger opening) to demonstrate magnetically-guided movement were performed in a 0.4 M hydrochloric acid solution. The magnetically-guided Ni/Ti/PANI/Zn microengines exhibited a speed of ~100 μm/s in this example. It is noted that the speed the exemplary Ni/Ti/PANI/Zn microengines was slower than that of the PANI/Zn microengines under the same conditions (e.g., 140 μm/s exhibited by the PANI/Zn microengines), e.g., reflecting the influence of the additional Ti/Ni layers on the gas-bubble propulsion mechanism.

Figure 12A:
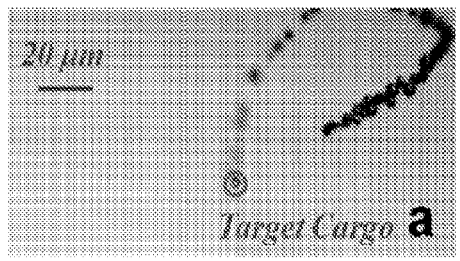
FIGS. 12A-12D show time lapse images showing the propulsion and cargo manipulation of an exemplary Ni/Ti/PANI/Zn microengine.
Figure 12C:
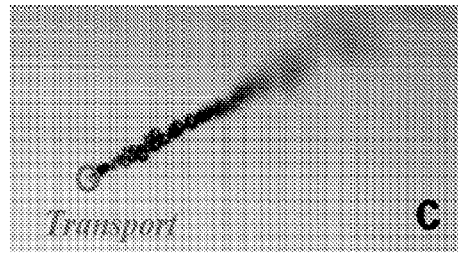
Figure 12B:
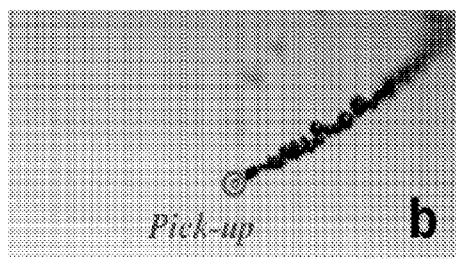
Figure 12D:
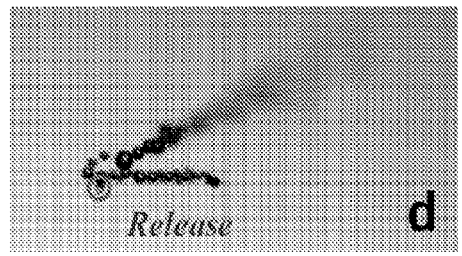

FIGS. 12A-12D show time lapse images that show the propulsion and cargo manipulation (e.g., load, drag, and drop) of an exemplary Ni/Ti/PANI/Zn microengine (e.g., having a 5 μm diameter at the larger opening). For example, FIG. 12A shows the exemplary Ni/Ti/PANI/Zn microengine approaching exemplary 5 μm target sphere cargo. FIG. 12B shows the exemplary Ni/Ti/PANI/Zn microengine capturing the cargo magnetically. FIG. 12C shows the exemplary Ni/Ti/PANI/Zn microengine transporting the cargo over a predetermined path. FIG. 12D shows the exemplary Ni/Ti/PANI/Zn microengine and releasing the cargo, e.g., by rapidly changing the direction the magnetic field direction. The exemplary fluid medium included 400 mM HCl solution containing 1.67% Triton X-100 (pH=0.4). For example, during the transporting operation, the speed of the exemplary Ni/Ti/PANI/Zn microengine decreased from 110 μm/s to 90 μm/s after capturing the polystyrene cargo, e.g., reflecting the increase fluid drag force exerted by the larger largo. For example, a drag force of ~5 pN can be estimated, by considering the microengine as a cylindrical nanorod as described above using Eq. (1).

Exemplary implementations to demonstrate direct locomotion of the acid-driven microengines in untreated biological environments have also been performed. For example, the movement of the $H_2$-bubble propelled PANI/Zn microengine in acidified human serum was determined to be 92 μm/s (e.g., over a 5 sec period). Thus, despite the raw biological medium (e.g., such as that of the human stomach), the exemplary PANI/Zn microengines can move rapidly, albeit at a slower speed (e.g., 92 μm/s as compared to 170 μm/s in the aqueous acid solution), e.g., which reflects the effects of a higher viscosity of human serum on the propulsion mechanism.

The results of the exemplary implementations demonstrated that the disclosed membrane template electrodeposition fabrication techniques can mass produce acid-driven microengines with various sizes and configurations, which can move at high speeds (e.g., >100 body lengths/s) within an acidic fluid without the presence of a fuel. Additionally, the results of the exemplary implementations demonstrated that the exemplary acid-driven microengines can propel well in diverse biological fluids (e.g., such as fluids-found in the stomach), as well as extreme acidic environments (e.g., such as silicon wet-etching baths). Thus, the disclosed microengines can be utilized in diverse biomedical and industrial applications, e.g., including motion-based pH sensing.

In another aspect, the disclosed technology can include nano/microstructures that can be functionalized to capture and transport substances or microorganisms. For example, the disclosed nano/microstructures can be configured as a microtube engine coated with a superhydrophobic molecular layer to enable the microtube to remove oil-based substances from a particular region in a fluid environment.

Oil is a major source of ocean pollution and ground water contamination. For example, the presence of oils in wastewaters as a product of various manufacturing processes is common in different industries. Episodes of major water pollution caused by oil spillage have resulted in the release of millions of tons each year. For example, the 1989 Exxon Valdez and 2010 Deepwater Horizon incidents spilled millions of gallons of crude oil. The removal of oils and organic solvents from contaminated water is thus of considerable importance for minimizing the environmental impact of these pollutants. Substantial efforts have thus been devoted to develop effective tools towards the remediation and clean-up of oil spills. However, most of the conventional methods lack selectivity and efficiency and are not cost-effective or environmental friendly.

Nanomachines and micromachines of the disclosed technology can be used to implement an oil collection method that includes capture, transport and removal of oil droplets. For example, the disclosed microtube engines can be modified with a superhydrophobic molecular layer able to adsorb oil by means of its strong adhesion to a long chain of self-assembled monolayers (SAMs) of alkanethiols created onto the rough outer surface (e.g., outer gold layer) of the microengine device. In some examples, the microtube engines can include a SAM-coated Au/Ni/PEDOT/Pt structure (e.g., the SAM layers having a polar-terminal group) that can exhibit continuous interaction with large oil droplets, capable of loading and transporting multiple small oil droplets. For example, the functionality of the exemplary SAM-coated Au/Ni/PEDOT/Pt microengines can be influenced based on the alkanethiol chain length, polarity and head functional group, which affect the surface hydrophobicity upon the oil-nanomotor interaction and the propulsion of the microengines.

For example, surfaces with superhydrophobic properties can repel water while strongly interacting with nonpolar or oily liquids, which firmly adhere to the superhydrophobic interfaces. For example, the micro-/nano-hierarchical texture and the chemical composition can be essential for promoting the superhydrophobic properties that are effective for oil removal, e.g. such as the surface polarity and roughness that affect the oil-surface interaction. SAMs formed by the spontaneous and strong chemisorption of alkanethiols on the outer surface (e.g., gold or silver surfaces) of the exemplary microtube engines can transform the microtubes into superhydrophobic interfaces. For example, hydrophilic surfaces can become superhydrophobic after exposure to particular SAM assemblies, e.g., such as an octadecanethiol. For example, tailoring the ending functional group and/or the length of an alkanethiol chain can control of the surface polarity of the SAM-modified microengines. For example, methyl-terminated SAMs can produce hydrophobic surfaces, while hydroxyl-terminated ones provide wettable surfaces.

The disclosed membrane-template electrodeposition techniques can be utilized for mass production of the exemplary superhydrophobic microtube engines. For example, template-fabricated catalytic microtubes can be configured to be superhydrophobic microtube engines, e.g., in which the catalytic microtube structure can include a polymer/Pt bilayer core (e.g., as shown in FIGS. 1A and 1B) with additional nickel and gold layers electrodeposited on the outside of the polymer/Pt bilayer to provide magnetic guidance and surface functionalization (e.g., with receptors), respectively. For example, the outer surface of the outer gold layer can be further modified with a SAM coating (e.g., including an alkanethiol molecular chain). For example, the, terminal functional groups of the attached SAM coating can be chemically modified to attach molecular bioreceptors, e.g., including, but not limited to, DNA probes, aptamers, antibodies and lectins.

Figures 13A, 13B:
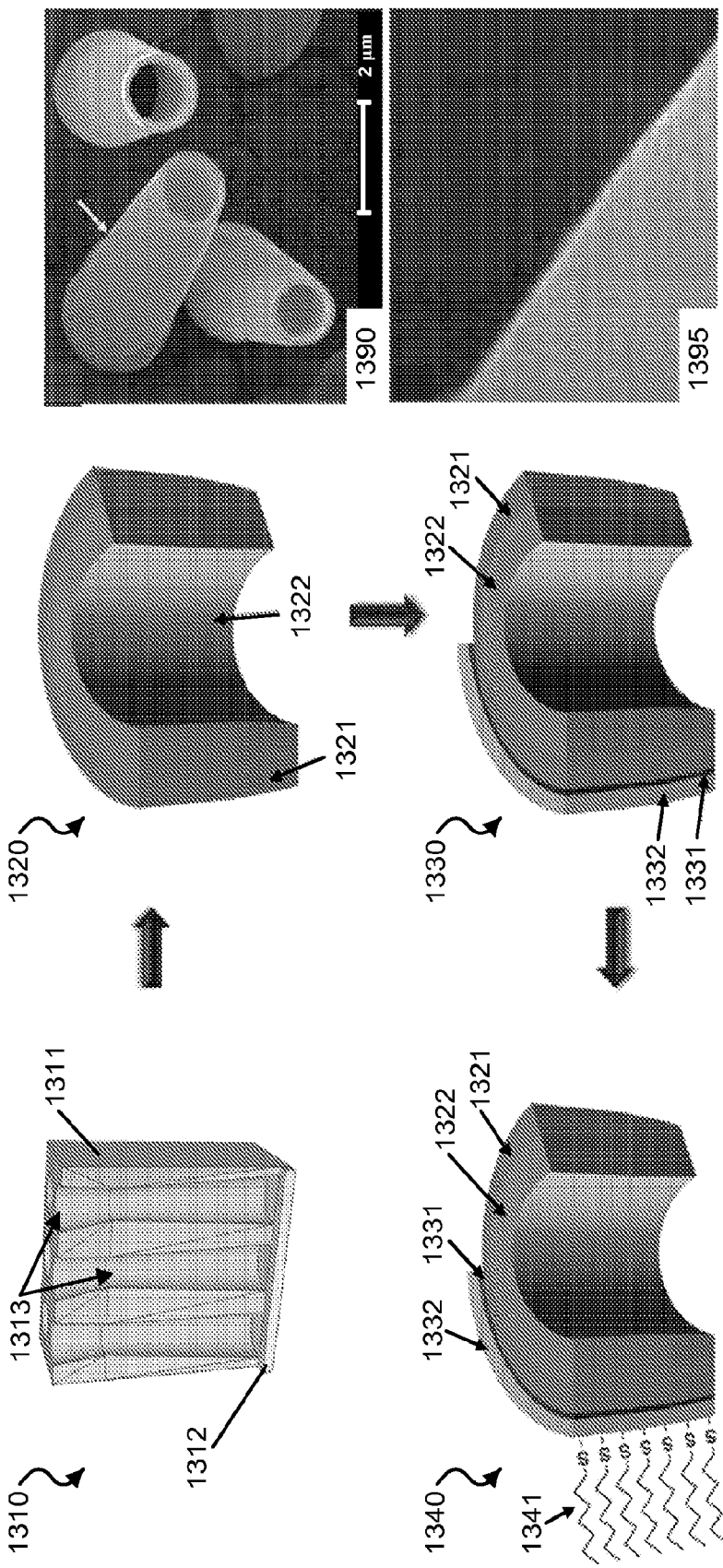
FIG. 13A shows a schematic diagram of an exemplary membrane-template electrodeposition fabrication process of functionalized microtube engines.
FIG. 13B shows SEM images of exemplary PEDOT/Pt microtube engines.

FIG. 13A shows a schematic diagram of an exemplary membrane-template electrodeposition fabrication and modification process for preparation of hydrophobic microtube engines of the disclosed technology, e.g., such as a dodecanethiol SAM-modified Au/Ni/PEDOT/Pt catalytic microengine. For example, the exemplary process includes a membrane-template mass production technique to produce multilayer microtube engines including a core bilayer microtube having a poly(3,4-ethylenedioxythiophene) (PEDOT) outer layer and platinum inner layer using porous membranes. Also, for example, the exemplary process includes coating techniques to form additional outer layers, e.g., including a nickel layer and a gold layer, over the core bilayer microtube structure, e.g., in which the exemplary Ni material layer can be used for magnetic steering and the Au layer can be used for modification of superhydrophobic monolayer coatings. The exemplary process can include a process 1310 to assemble a porous membrane 1311 having conical pores 1313 to a substrate 1312. For example, the process 1310 can include sputtering a layer of a conductive material onto one porous side of the membrane 1311 to form the substrate 1312. In some examples, the membrane 1311 can include a cyclopore polycarbonate membrane with a 20 μm thickness having an asymmetrical double cone pore structure with a 2 μm diameter at both openings and a 1 μm diameter as a minimum diameter internally within the pores 1313. In other examples, the membrane 1311 can include single conical pores (e.g., with a 1 μm diameter at one opening and a 2 μm diameter at other opening). The substrate 1312 can include an electrically conductive material, e.g., such as gold. The assembled porous membrane-substrate can be used as a working electrode, e.g., in electroplating processes.

In FIG. 13A, the exemplary membrane-template electrodeposition process can include a process 1320 to deposit an outer layer 1321 (e.g., of a polymer material, including PEDOT) within the pores 1313 of the membrane 1311, followed by deposition of an inner layer 1322 (e.g., a catalytic material including Pt) to form a bilayer core microtube structure within the pores 1313 of the membrane 1311. For example, 3,4-ethylenedioxythiophene can be electropolymerized into the pores 1313 of the membrane 1311, in which PEDOT can grow as a tube structure, e.g., due to coupling of oxidized monomers that bind to the negatively charge wall of the membrane 1311. For example, 3,4-ethylenedioxythiophene monomers can polymerize on the inner wall of the membranes due to solvophobic effects and electrostatic effects, leading to a rapid formation of a PEDOT film. For example, a platinum layer can be subsequently plated along the inner surface of the polymer layer 1321 (e.g., the PEDOT layer) using a galvanostatic method. For example, the high conductivity property of poly(3,4-ethylenedioxythiophene) in acid conditions can provide support for platinum deposition, leading to a formation of the bilayer tube structure of platinum inside the PEDOT layer within membrane pores. Subsequently, the exemplary membrane-template electrodeposition process 1320 can also include a process to dissolve the membrane 1311 and release of the core bilayer microtubes. For example, dissolution of the membrane 1311 can include the use of methylene chloride, among other organic solvents.

The exemplary fabrication process in FIG. 13A can include a process 1330 to deposit at least one outer layer over the outer surface of the core bilayer microtubes. For example, a magnetic material layer 1331 (e.g., such as a Ni layer) can be deposited over the outer surface of the core bilayer microtubes by e-beam vapor deposition. The exemplary Ni layer can provide the magnetic steering and navigation control functionality to the microtube engines. For example, subsequently, an outer functionalization material layer 1332 (e.g., such as an Au outer layer) can be deposited over the magnetic material layer 1331 by e-beam vapor deposition. In some implementations, the selected magnetic material to serve in the magnetic material layer 1331 can also provide the functionality to enable further surface functionalization, e.g., such as binding monolayers such as superhydrophobic SAMs, such that the deposition of the outer functionalization material layer 1332 may not be implemented.

Still referring to FIG. 13A, the exemplary fabrication process can include a process 1340 to form a chemical coating 1341 having superhydrophobic properties, e.g., by self-assembly of long alkanethiols chains on the rough outer surface of the functionalization material layer 1332. For example, the chemical coating 1341 can include an alkanethiol SAM layer formed on an exemplary gold layer 1332 of the microengine surface by incubation of the microtubes in a 0.5 mM n-dodecanethiol ethanol solution for 30 min. The chemical coating 1341 can include a variety of chemical structures that exhibit hydrophobic properties, such as alkanethiols, e.g., including hexanethiol (C-6), dodecanethiol (C-12) and octadecanethiol (C-18), among others.

FIG. 13B shows an SEM image 1390 of the exemplary PEDOT/Pt microengines, including an image 1395 showing a zoomed-in view of the outer surface zone identified in the image 1390 by the arrow. For example, the SEM images 1390 and 1395 of the unmodified microengine indicate a rough surface, e.g., characteristic of nitrate-doped PEDOT films.

Figure 13C:
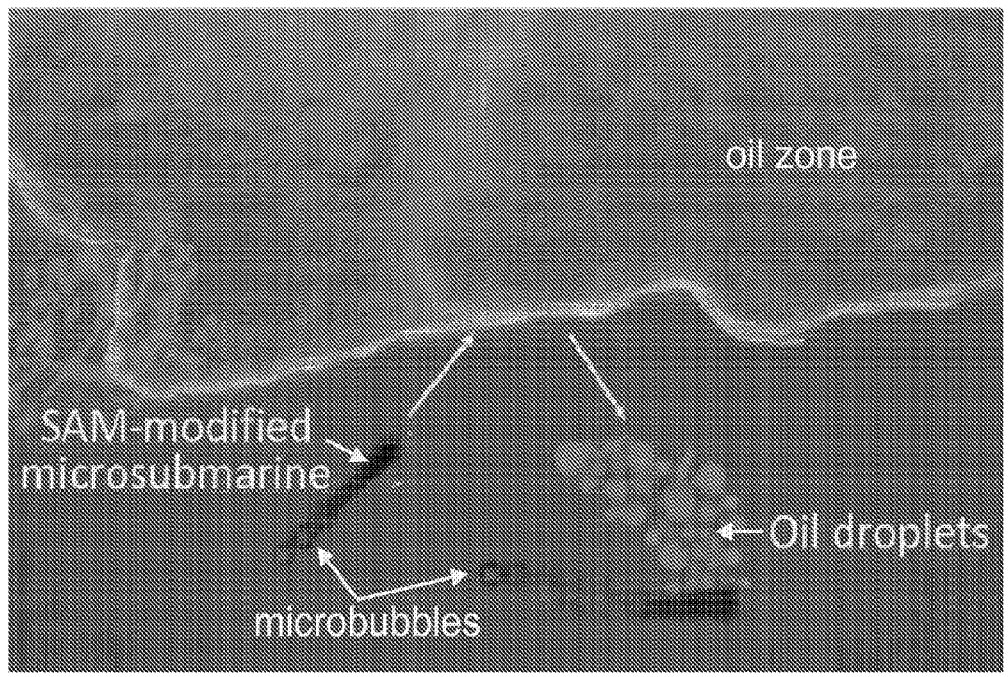
FIG. 13C shows an illustrative picture demonstrating the oil removal functionality of SAM-modified catalytic microtube engines.

The exemplary method shown in FIG. 13A can be implemented to produce SAM-modified microtube engines able that strongly interact with oily liquids via adhesion and permeation onto its long alkanethiol coating. FIG. 13C shows an illustrative picture demonstrating this functionality in an oil removal application. The relative similar dimensions of microengine and oil droplets (which range from ~1 to ~100 μm, depending on the emulsion composition) permit convenient real-time optical visualization of the oil-microengine interaction. For example, the template-prepared PEDOT/Pt microtubes can propel efficiently in different media via the expulsion of oxygen bubbles generated from the catalytic oxidation of hydrogen peroxide fuel along their inner Pt layer. It is noted, for example, that the speed of the polymer/Pt microengines (e.g., such as the PEDOT/Pt microengines) is reduced by up to 50% after the subsequent deposition of the outer magnetic and functionalization layers, e.g., which may reflect partial blocking of the inner Pt catalytic layer. However, this exemplary reduced speed is still sufficient for transporting large cargos. Table 2 summarizes the average speeds of the microengines at each stage of the formation of the different layers involved in the fabrication process and oil removal applications.

TABLE 2

| Microengine type | Speed (μm/s) |
| --- | --- |
| PEDOT/Pt | 420 |
| Au/Ni/PEDOT/Pt | 200 |
| SAM/Au/Ni/PEDOT/Pt | 105 |
| SAM/Au/Ni/PEDOT/Pt/few (1-5) droplets | 20-50 |
| SAM/Au/Ni/PEDOT/Pt/numerous droplets | 10-20 |

Exemplary fabrication processes and implementations were performed to demonstrate the uniform and efficient production and the functionalities and capabilities of the disclosed superhydrophobic microengine technology. For example, SAM-functionalized multilayer catalytic microtubes were prepared using the described membrane template-directed electrodeposition and functionalization process. For example, exemplary implementations using fabricated dodecanethiol-coated Au/Ni/PEDOT/Pt microengines were performed to demonstrate an effective capture and transport of oil droplets from aqueous media. For example, the influence of the alkanethiol chain length upon the oil-nanomotor interaction and the collection efficiency was examined in these exemplary implementations, e.g., by applying various chemical coatings using SAMs of different chain lengths, e.g., hexanethiol (C-6), dodecanethiol (C-12) and octadecanethiol (C-18).

For example, SAM-modified Au/Ni/PEDOT/Pt catalytic microengine were fabricated using an exemplary cyclopore polycarbonate template membrane, e.g., containing 2 μm maximum diameter conical-shaped micropores (Catalog No 7060-2511; Whatman, Maidstone, UK). For example, a 75 nm gold film was first sputtered on one side of the exemplary porous membrane to serve as working electrode using the Denton Discovery 18. The sputter was performed at room temperature under vacuum of 5×10⁻⁶ Torr, DC power 200 W and flow Ar to 3.1 mT (e.g., with rotation speed of 65 and sputter time 90 s). A Pt wire and an Ag/AgCl with 3 M KCl were used as counter and reference electrodes, respectively. The exemplary porous membrane-substrate device was then assembled in a plating cell with an aluminum foil serving as contact. For example, PEDOT microtube structures were electropolymerized up to 0.1 C at +0.80 V from a plating solution containing 15 mM EDOT monomer, 50 mM SDS and 7.5 mM $KNO_3$. The inner Pt tube of the core bilayer microtube structure was deposited galvanostatically at −2 mA for 600 s from a platinum plating solution (Platinum RTP; Technic Inc, Anaheim, Calif.). For example, the sputtered gold layer substrate was completely removed, e.g., by mechanical hand polishing with 3-4 μm alumina slurry. The exemplary bilayer core microtubes were collected by centrifugation at 6000 rpm for 3 min and washed repeatedly with methylene chloride, followed by ethanol and ultrapure water (e.g., 18.2 MΩcm), three times of each, with a 3 min centrifugation following each wash. The exemplary bilayer core microtubes suspension was then evaporated onto glass slides prior to the sequential deposition of 10 nm Ti (e.g., acting as an adhesion layer), 15 nm Ni (e.g., to form the exemplary magnetic layer 1331), and 15 nm of Au (e.g., to form the exemplary functionalization layer 1332) over the exemplary bilayer core microtubes by using electron beam deposition.

The external surface of the Au functionalization layer 1332 was subsequently modified by immersion in a 0.5 mM dodecanethiol in absolute ethanol, after which the resulting monolayer-modified microengine were washed with Milli-Q water and isolated by centrifugation at 6000 rpm for 4 min. The exemplary implementations were carried out at room temperature. Characterizations of the chemical structure effect, e.g., length chain and terminal groups, on the speed were performed with different thiols, e.g., including hexanethiol, mercaptohexanol, dodecanethiol and octadecanethiol, dissolved in ethanol. Non-functionalized (bare) microengines without the monolayer were also prepared, e.g., to serve as control groups in exemplary experimental implementations.

For example, template electrochemical deposition of microtube was carried out with a CHI 661 D potentiostat (CH Instruments, Austin, Tex.). An inverted optical microscope (Nikon Eclipse Instrument Inc. Ti-S/L100), coupled with a 40× objective, using a Hamamatsu digital camera C11440 and a NIS-Elements AR 3.2 software, were used for capturing movies at a frame rate of 20 frames per second. The speed of the microengines was tracked using a NIS-Elements tracking module and the results were statistically analyzed using Origin software.

The exemplary experimental implementations included preparing an emulsion containing milliQ water/oil sample/6% sodium cholate (NaCh) (2:2:1), e.g., in order to self-propel the catalytic microengines around different oil droplets or capturing such droplets. For example, a known volume of this solution was spread on a glass slide and an equal volume of a solution containing the microengines and the same volume of hydrogen peroxide was added to get a final concentration of 0.4% NaCh and 10% $H_2O_2$. The exemplary experimental implementations were performed using olive and motor oils dispersed in Milli-Q water. For example, initial implementations were carried out with Nile-red stained olive oil for improved visualization under the microscopy. However, the exemplary dye was not used in many subsequent implementations as the water-oil interface was sufficiently distinguishable without such staining.

Figure 14A:
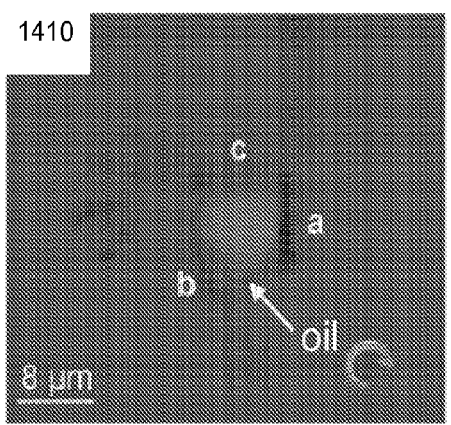
FIGS. 14A and 14B show images of exemplary SAM-modified and unmodified microengines in the presence of oil droplets within a fluid.
Figure 14B:
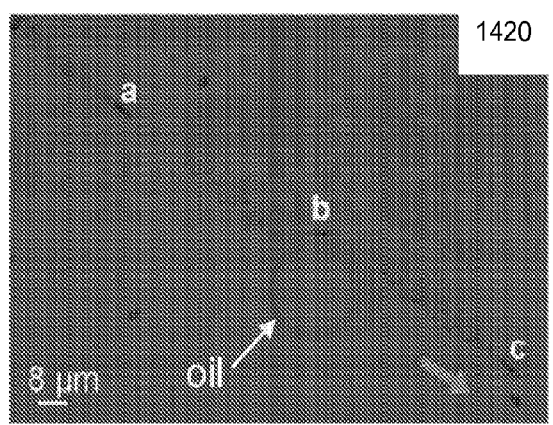

FIGS. 14A and 14B show images of exemplary SAM-modified and unmodified microengines in the presence of a stained olive oil droplet attached to a glass slide within a fluid. For example, the fluid included fuel conditions of 0.4% NaCh and 10% $H_2O_2$. FIG. 14A shows an image 1410, taken from video images in a single overlaid image, of an exemplary oil collection method by exemplary SAM-modified catalytic microengines. The exemplary SAM-modified catalytic microengines included dodecanethiol-modified Au/Ni/PEDOT/Pt microtubes. As shown in FIG. 14A, the exemplary oil collection method includes a step (a) of the superhydrophobic catalytic microengine approaching an oil source, a step (b) of the superhydrophobic catalytic microengine making contact with the oil source, and a step (c) of the superhydrophobic catalytic microengine spinning around the oil source. FIG. 14B shows an image 1420, taken from video images in a single overlaid image, demonstrating the failure of unmodified catalytic microengines to collect oil droplets from the oil source. As shown in FIG. 14B, the unmodified catalytic microengine approached the oil source (a), made partial contact with the oil source (b), and left the oil source (c) without substantial oil-microengine interaction. The exemplary arrows in FIGS. 14A and 14B indicate the microengine trajectory.

For example, as shown in FIG. 14A, the strong interaction between the SAM-modified microengine and an oil droplet resulted in a continuous spinning of the SAM-modified microengine around the droplet with an accelerated speed ranging up to 200 μm/s, which occurred even after a prolonged 20 min period. These exemplary data also confirmed that the exemplary hydrogen peroxide fuel and the sodium cholate (NaCh) surfactant did not compromise its interaction with the oil droplet or the integrity of the attached SAM. In contrast, for example, no such interaction was observed using the unmodified microengine (as shown in FIG. 14B), e.g., in which the bare Au/Ni/PEDOT/Pt micromotor moved rapidly past the oil droplet.

Figures 15A, 15B, 16A, 16B:
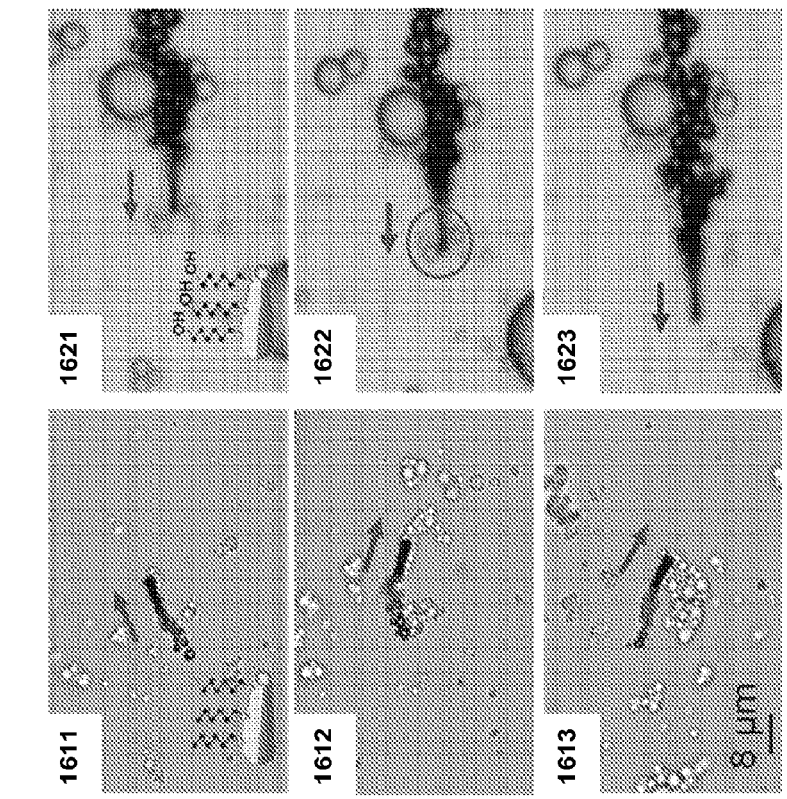
FIG. 15A shows a set of images showing the capture and transport of multiple small olive oil droplets by an exemplary dodecanethiol-modified Au/Ni/PEDOT/Pt microengine.
FIG. 15B shows a data plot displaying the dependence of speed upon the number of transported oil droplets by exemplary SAM-modified microengines.
FIGS. 16A and 16B show images of exemplary hexanethiol-modified microengines with different head functional groups interacting with oil droplets.

Efficient capture and transport of oil droplets was also observed when the exemplary SAM-modified catalytic microengines navigated in contaminated water samples containing small 'free-floating' oil droplets. FIG. 15A shows a set of images 1510 showing the capture and transport of multiple small olive oil droplets by an exemplary dodecanethiol-modified Au/Ni/PEDOT/Pt microengine. The image set 1510 includes video images taken after navigating in a fluid containing oil droplets and a 10% fuel solution for 5, 12, 66 and 80 s. For example, it was observed that the longer the navigation time, the more oil droplets were collected and confined onto the surface of the self-propelled micromotor. For example, around 5 droplets (1.7±0.4 μm size) were captured and transported (as shown in the image a of the image set 1510) after 5 s of navigation, and around 40 droplets were attached to the motor surface following 80 s of navigation (as shown in the image d of the image set 1510). The exemplary data shown in the image set 1510 demonstrate that these SAM-modified microengines provide high towing force for transporting efficiently approximately 10-fold their volume.

For example, the increased drag force (Stokes's law) resulted in a decrease in speed of the oil-towing micromachines upon increasing the cargo size (e.g., number of captured droplets). This is illustrated in a data plot 1550 shown in FIG. 15B that displays the dependence of the microengine speed upon the number of transported oil droplets. The data plot 1550 also includes an illustrative schematic 1551 of an exemplary dodecanethiol-modified microengine. As shown in FIG. 15B, the speed rapidly decreased from 26 μm/s to 12 μm/s upon increasing the number of oil droplets from 7 to 30, and then more slowly to 11 μm/s for 43 oil droplets.

The disclosed technology can include techniques to tailor the polarity of the microengine surface, e.g., which can be based on the chain length of an n-alkanethiol coating, and hence altering the capture and transport properties of the engineered microengines. For example, chain length, head groups, preparation time and other conditions (e.g., temperature) can give rise to different SAM packing densities, configurations, and polarity.

Examination was conducted on the influence of the SAM head group and surface polarity on the microengines-oil interaction, by comparing the behavior of microengines coated with C6 SAM containing methyl and hydroxyl terminal groups using different time scales. FIGS. 16A and 16B show images of exemplary C6-SAM-modified microengines with different head functional groups interacting with small olive oil droplets. FIG. 16A shows time lapse images 1611, 1612, and 1613 of hexanethiol-modified microengines capable of confining a payload of multiple oil droplets, corresponding to navigation times of 11, 50, and 73 sec, respectively. FIG. 16B shows time lapse images 1621, 1622, and 1623 of mercaptohexanol-modified microengines incapable of picking up such oil droplets, corresponding to navigation times of 6.57, 6.66, and 6.71 sec, respectively. The exemplary images 1611 and 1621 include illustrative schematics of the respective SAM-modified microengines, e.g., hexanethiol-modified microengines in the image 1611 and mercaptohexanol-modified microengines in the image 1621. The exemplary arrows shown in the images of FIGS. 16A and 16B indicate the direction of the microengine movement.

As shown in the FIGS. 16A and 16B, the polarity of the head functional group of the attached chemical coating strongly influenced the interaction between the exemplary modified microengines and the oil droplets. For example, as shown in FIG. 16A, small oil droplets attached to the hexanethiol-modified microengine upon locomoting in the fluid sample. In contrast, for example, as shown in FIG. 16B, the mercaptohexanol-modified microengines did not interact with the large or small oil droplets after rapidly contacting them, e.g., even after prolonged locomotion of the mercaptohexanol-modified microengines within the fluid.

Figure 17:
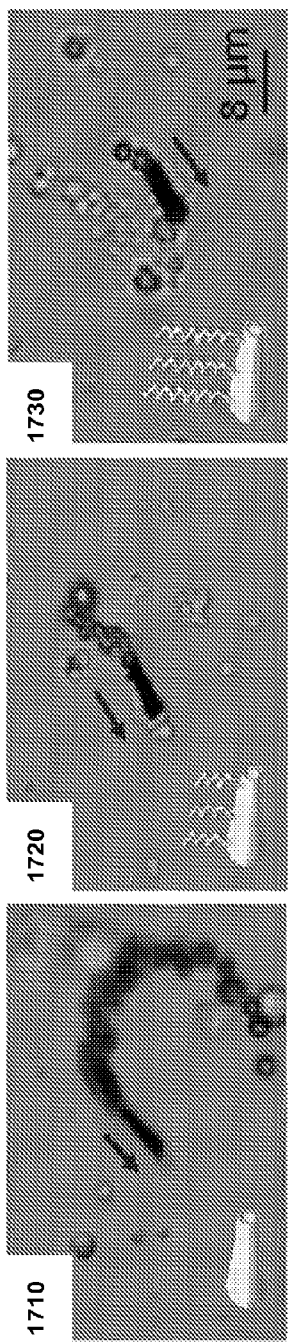
FIG. 17 shows images showing the effect of thiol length chain on SAM-modified microengine-oil interaction.

The exemplary implementations included examination of the influence of the alkanethiol chain length upon the oil-nanomotor interaction, e.g., by modifying the microengines with SAMs of different alkanethiol lengths (e.g., C6, C12 and C18). FIG. 17 shows images 1710, 1720, and 1730 showing the effect of thiol length chain on the SAM-modified microengine-oil droplets interaction. For example, the image 1710 shows an exemplary unmodified microengine, the image 1720 shows an exemplary microengine modified with hexanethiol, and the image 1730 shows an exemplary microengine modified with dodecanethiol. The exemplary images of FIG. 17 were taken after approximately the same time of navigation in the fuel solution (e.g., 10% $H_2O_2$ with 0.4% NaCh). The exemplary arrows indicate the direction of the microengine movement.

As shown in the FIG. 17, the alkanethiol chain length of the attached chemical coating strongly influenced the interaction between the exemplary modified microengines and the oil droplets. For example, the C12-modified microengine exhibited strong microengine-oil interaction (e.g., shown in the image 1730 in which the C12-modified microengine spins around a large olive oil droplet), as compared to the weaker interaction experienced by the C6-modified micromotor (e.g., shown in the image 1720 in which the C6-modified microengine did not spin around the droplet). For example, the C12-modified microengine exhibited a higher number of captured oil droplets, e.g., as compared to the lower number of droplets attached to the C6-modified motor and to the absence of captured droplets using the unmodified microengine. The exemplary data are consistent with the surface wettability properties (e.g., determined by contact angle measurements) of n-alkanethiols of different lengths. For example, based on the higher hydrophobic character of long chain thiols, C18 SAM-coated microengines can offer higher oil-adsorption capabilities. However, a tradeoff between oil-absorption ability and speed may exist within the chemical coatings including longer alkanethiol chains. For example, the exemplary C18-SAM modified microengines exhibited slower motion which may be due to greater blocking of their inner Pt catalytic layer in the presence of longer alkanethiols.

Figure 18:
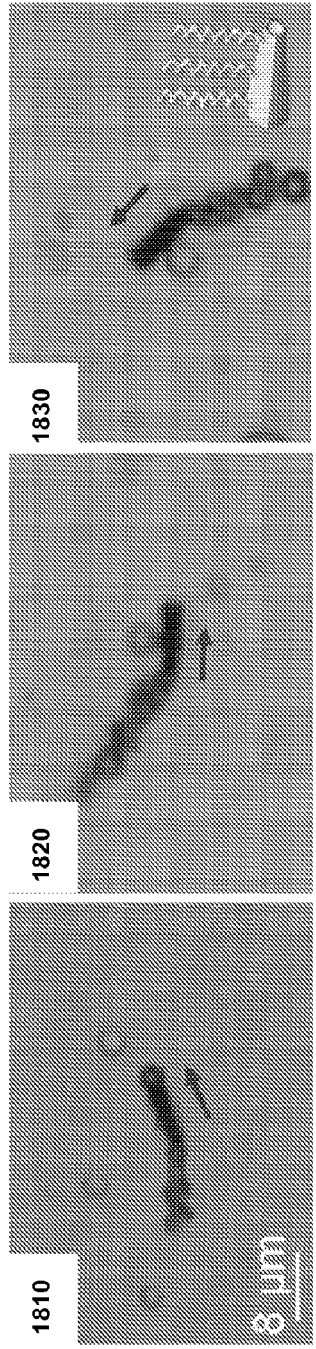
FIG. 18 shows time lapse images of an exemplary dodecanethiol-modified microengine in an oil-contaminated water sample.

FIG. 18 shows time lapse images of an exemplary dodecanethiol-modified microengine collecting and transporting floating droplets motor oil in a fuel-enhanced oil-contaminated water sample. For example, the fluid included fuel conditions of 0.4% NaCh and 10% $H_2O_2$, and the time lapse images were taken from video images after 78 s of navigation. The exemplary time lapse images of FIG. 18 show the microengine approaching (image 1810), contacting (image 1820), and carrying (image 1830) the motor oil droplets. The image 1830 in FIG. 18 includes an inset of a schematic of the exemplary dodecanethiol-modified microengine. The exemplary arrows indicate the direction of the microengine movement. The SAM-coated microengines displayed an 'on the fly' capture upon contacting the small droplets of motor oil that were floating in the contaminated water sample. These results exemplify the capability of the superhydrophobic-modified microengines for facile, rapid and high efficient collection of oils in oil-contaminated water samples.

For example, the extent of the micromotor-oil interaction and the collection efficiency can be tuned by controlling the surface hydrophobicity of the microengines, e.g., through the use of different chain lengths and head functional groups. The disclosed microengines are capable of collecting and transporting oil substances through strong interactions between the chemically-modified superhydrophobic coatings and large oil source, and/or by the collection and transport of multiple free-floating small oil droplets of an oil source, e.g., present in a contaminated water sample. For example, these micromotor-oil interactions can be utilized in the suitable final disposition of oily wastes (or other organic solvents) by collecting them in a controlled fashion within a certain spatially separated zone. For example, simultaneous parallel movement of multiple SAM-modified microengines can be implemented to improve the efficiency of oil-removal processes. For example, practical large-scale oil cleaning operations can utilize the disclosed nano/micromotors propelled by their own natural environment or driven by an external (magnetic or electrical) control. In addition, for example, the disclosed superhydrophobic microengines can be used for the isolation of hydrophobic molecules, e.g., drugs, and for transferring target analytes between liquid-liquid immiscible interfaces, or other applications in diverse analytical microsystems. The disclosed SAM-modified microengines can include multifunctional coatings of mixed chemically-functional layers or multiple chemically-functional layers, e.g., coupling the exemplary hydrophobic compounds with additional functions (e.g., biocatalysis) into the SAMs. For example, biocatalyst-superhydrophobic microengines can be implemented in 'capture and destroy' operations in a variety of biomedical applications.

In another aspect, the disclosed technology includes chemically-powered nanoscale bilayer motors configured using various outer layer materials and inner catalytic materials.

The disclosed membrane template electrosynthesis techniques can be varied to produce a variety of polymer/metal, semiconductor/metal (e.g. $TiO_2$, ZnO, $SiO_2$, $Al_2O_3$), and metal/metal bilayer nanomotors and micromotors, e.g., using on different materials and synthesis conditions, to engineer their morphology and composition to enhance their functionality (e.g., propulsion capabilities). For example, the exemplary template-directed electrochemical synthesis methods include the ability to control the morphology of the structures.

For example, the influence of the composition and electropolymerization conditions upon the propulsion of new template-prepared polymer-based bilayer microtubular microengines is described. Exemplary implementations were performed to evaluate the effects of different electropolymerized outer layers, e.g., including polypyrrole (PPy), poly(3, 4-ethylenedioxythiophene) (PEDOT), and polyaniline (PANI), as well as various inner layer catalytic metal surfaces (e.g., Ag, Pt, Au, and Ni—Pt alloy), upon the movement of the exemplary bilayer microtubes. Microtube engines of the varying configurations of electropolymerized outer layers and metallic and alloy inner layers were compared. For example, electropolymerization conditions including the monomer concentration and medium (e.g., surfactant, electrolyte) can affect the morphology and locomotion of the fabricated microtubes. For example, the movement can be influenced by the choice of monomer structure, e.g., which can affect the diameter and shape. The inner layer surface can be engineered with an alloyed material (e.g., Pt—Ni alloy) to provide magnetic control and catalytic fuel decomposition within one layer, e.g., simplifying the preparation of magnetically-guided microengines. Also, for example, polymer-based micromotors having an inner gold layer can produce efficient biocatalytic propulsion in low peroxide levels, e.g., in connection to an immobilized catalase enzyme.

For example, conducting polymers, such as polyaniline (PANI), polypyrrole (PPy), polythiophene (PT) and poly(3, 4-ethylenedioxythiophene) (PEDOT) can provide advantages to the fabricated bilayer microtube structures, e.g., based on their light weight, conductivity, mechanical flexibility, unique chemical and redox properties, minimal structural defects, high aqueous stability, and biocompatibility. For example, functionalized-polymer microstructures can be used in microscale actuators, drug carriers or metabolite and genetic biosensors. The exemplary conducting polymer materials can be employed in the disclosed nano/microtube structures, e.g., such as the exemplary self-propelled microengines of the present technology, which can be prepared by the described electropolymerization techniques. Implementation of these exemplary electropolymerization techniques can offer precise control of the deposition conditions and hence of the dimensions and morphology of the resulting fabricated microtubes. For example, the exact microstructure dimensions and morphologies of the resulting conducting polymers can affect the physical and chemical properties.

Exemplary implementations were performed to demonstrate the influence of the composition and electropolymerization conditions of the disclosed fabrication processes on the functionalities and capabilities of the disclosed microengine technology.

For example, various microtube structures were prepared using the exemplary template-directed electrodeposition techniques (e.g., such as those shown in FIG. 1A and FIG. 13A). For example, an exemplary cyclopore polycarbonate membrane, e.g., containing 2 μm diameter conical-shaped micropores, was employed as the template. For example, a 75 nm gold film was first sputtered on one side of the porous membrane to serve as working electrode using the Denton Discovery 18. The sputter was performed at room temperature under vacuum of $5 \times 10^{-6}$ Torr, DC power 200 W and flow Ar to 3.1 mT (e.g., with rotation speed of 65 and sputter time 90 s). A Pt wire and an Ag/AgCl with 3 M KCl were used as counter and reference electrodes, respectively. The exemplary porous membrane-substrate device was then assembled in a plating cell with an aluminum foil serving as contact. PANI microtubes were prepared by implementing the following steps. For example, aniline and pyrrole were distilled before use at a vapor temperature of 100° C. and a pressure of 13 mmHg. The nucleation and growth of conducting polymer microtubes involve electrostatic and solvophobic interactions between the polymers and pore wall. PANI microtubes were electropolymerized at +0.80 V for 0.02 C from a plating solution containing 0.1 M $H_2SO_4$, 0.5 M $Na_2SO_4$ and 0.1 M aniline, and subsequently, the inner Pt tube was deposited galvanostatically at −2 mA for 1800 sec from a platinum plating solution (Platinum RTP; Technic Inc, Anaheim, Calif.). PEDOT microtubes were electropolymerized at +0.80 V for a charge of 0.06 C from a plating solution containing 15 mM EDOT, 7.5 mM $KNO_3$ and 100 mM sodium dodecyl sulfate (SDS), and subsequently, the inner Pt tube was deposited galvanostatically at −2 mA for 1800 sec. For example, the smaller microtubes (e.g., 4 μm in length) were synthesized using an exemplary cyclopore polycarbonate membrane, e.g., containing 1 μm diameter micropores. The exemplary PEDOT microtubes were electropolymerized at +0.80 V using a charge of 0.04 C while the corresponding inner platinum layer was deposited galvanostatically at −2 mA for 1000 sec. Polypyrrole (PPy) microtubes were electropolymerized at +0.80 V for a charge of 0.8 C from a plating solution containing 37 mM pyrrole and 7.5 mM $KNO_3$. Subsequently, for example, a metal microtube layer was plated inside the polymer layer. For example, different metallic layers were plated in different polymer microtubes using the disclosed membrane template electrosynthesis techniques. For example, for the exemplary PPy/Pt bilayer microtubes, the inner Pt tube layer was deposited galvanostatically at −2 mA for 1800 sec from a platinum plating solution (Platinum RTP; Technic Inc, Anaheim, Calif.). For example, for the exemplary PPy/Ag bilayer microtubes, silver was plated subsequently at −0.9 V (vs. Ag/AgCl) for a total charge of 1 C using a silver plating solution (1025 RTU @ 4.5 Troy/gallon; Technic Inc., Anaheim, Calif.). For example, for the exemplary PPy/Pt—Ni alloy bilayer microtubes, platinum-nickel alloy was plated at −1 V for a total charge of 2 C using a 1:1 mixed solution of a platinum solution and a nickel plating solution containing 20 g/L $NiCl_2.6H_2O$, 515 g/L $Ni(H_2NSO_3)_2.4H_2O$, and 20 g/L $H_3BO_3$. For example, for the exemplary PPy-Au, gold was plated at −0.9 V for 1 C from a gold plating solution (Orotemp 24 RTU RACK; Technic Inc.).

For example, the exemplary sputtered gold substrate was completely removed by hand polishing with 3-4 μm alumina slurry. The membrane was then dissolved in methylene chloride for 10 min to completely release the microtubes. The exemplary microtubes were collected by centrifugation at 6000 rpm for 3 min and washed repeatedly with methylene chloride, followed by ethanol and ultrapure water (e.g., 18.2 MΩcm), three times of each, with a 3 min centrifugation following each wash. The exemplary microtubes were stored in ultrapure water at room temperature when not in use.

The exemplary inner Au layer from the bilayer microtubes can be functionalized with monolayers, e.g., such as a mixed MUA/MCH monolayer. For example, a solution of 2.5 mM MUA and 7.5 mM MCH was prepared in ethanol. The exemplary microtube engines were incubated in the solution overnight. After rinsing the tubes with ethanol for 5 min, they were transferred to an Eppendorf vial containing a 200 μl ethanol solution with the coupling agents 1-Ethyl-3-[3-dimethylaminopropyl]carbodiimide hydrochloride (EDC), N-hydroxylsulfosuccinimide (Sulfo-NHS) at 0.4 M and 0.1 M respectively, and the enzyme catalase (2 mg mL$^{-1}$). This incubation was carried out 7 hours at 37° C. and thereafter rinsed with PBS with a pH of 7.4 and SDS 0.05 wt % for 15 min at each step. Finally the exemplary microengines were washed repeatedly by centrifugation at 6000 rpm for 3 min with water for three times to remove extra catalase in solution before testing.

For example, template electrochemical deposition of the exemplary microtubes was carried out with a CHI 661 D potentiostat (CH Instruments, Austin, Tex.). SEM images were obtained with a Phillips XL30 ESEM instrument, e.g., using an acceleration potential of 20 kV. Mapping analysis was investigated by Oxford EDX attached to SEM instrument and operated by Inca software. An inverted optical microscope (Nikon Instrument Inc. Ti-S/L100), coupled with a 40× objective, a Photometrics QuantEM 512/SC camera (Roper Scientific, Duluth, Ga.) and MetaMorph 7.6 software (Molecular Devices, Sunnyvale, Calif.) were used for capturing movies at a frame rate of 30 frames per sec. The exemplary speed data of the microengines were tracked using a Metamorph tracking module and the results were statistically analyzed using Origin software. For example, in order to self-propel catalytic microtube engines, aqueous hydrogen peroxide solutions (Sigma-Aldrich, cat. 95313) with concentrations ranging from 0.5-15.0% were used as chemical fuels, e.g., containing 2-5.0% (w/v) sodium cholate (Sigma-Aldrich, St Louis, Mo.) to reduce the surface tension.

Figure 19A:
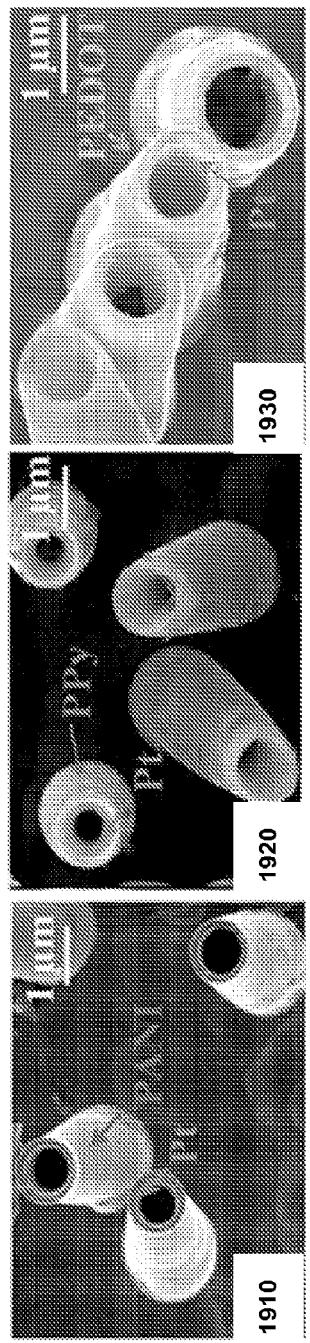
FIG. 19A shows SEM images of polymer-based template growth of exemplary bilayer microtubes.

FIG. 19A shows SEM images of polymer-based template growth of exemplary PANI/Pt bilayer microtubes (image 1910), exemplary PPy/Pt bilayer microtubes (image 1920), and exemplary PEDOT/Pt bilayer microtubes (image 1930). The thickness, and hence opening size, and the length of the polymer-based microtubes depend on the synthesis conditions. For example, PPy and PEDOT were electrosynthesized at +0.8 V using 7.5 mM KNO$_3$ as the electrolyte, and charges of 0.8 C and 0.06 C, respectively; PANI was electropolymerized using the same potential in a plating solution containing 0.1 M H$_2$SO$_4$, 0.5 M Na$_2$SO$_4$ and 0.1 M aniline for a charge of 0.02 C. The presence of HSO$_4^-$ anion, acidic media, and sodium cations can provide a high PANI polymerization rate, conductivity and electroactivity. The electropolymerization of PPy and PEDOT involved plating solutions containing the sodium dodecyl sulfate (SDS) surfactant for improving the monomer solubility in aqueous solution and lowering the oxidation potential resulting in improved the opening size and surface morphology of the microtubes. The images of FIG. 19A, involving these three different monomers, indicate that the disclosed template electrodeposition method leads to bilayer microtubes with uniform morphology. The exemplary PANI/Pt microtubes (shown in the image 1910), PPy/Pt microtubes (shown in the image 1920) and PEDOT/Pt microtubes (shown in the image 1930) were configured to a length of ~7 μm and were characterized with different front opening diameters of 0.8 μm, 0.6 μm and 1 μm, respectively. These exemplary different opening sizes can be attributed to differences in the sizes of the polymer chains, electropolymerization rate and in the packing patterns of the different polymers.

Figure 19B:
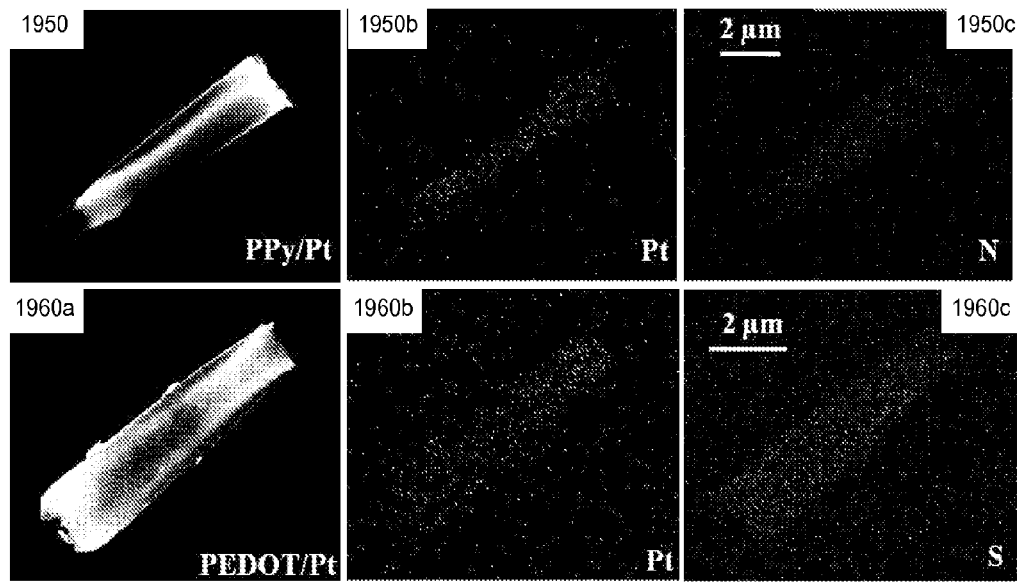
FIG. 19B shows images of an EDX analysis of exemplary polymer-based bilayer microtubes.

The morphological features of the polymer films exhibited a profound effect upon their electrochemical and electrochromic properties. For example, comparing the formation of the PANI-, PPy-, and PEDOT-based structures, the PANI and PEDOT microtubes exhibited a larger opening and did not close up, e.g., even after a long polymerization time. In contrast, for example, the PPy microtubes usually have a thicker layer, and form wire or fibers after long polymerization time, filling the pores completely. Exemplary EDX mapping analysis, shown in FIG. 19B, confirmed the presence of Pt, N of the exemplary PPy/Pt microtubes and Pt, S of the exemplary PEDOT/Pt microtubes, and the growth of the bilayer microtubes. FIG. 19B shows images 1950 of the EDX analysis results of the PPy/Pt microtubes and images 1960 of the EDX analysis results of the PEDOT/Pt microtubes.

Figure 20:
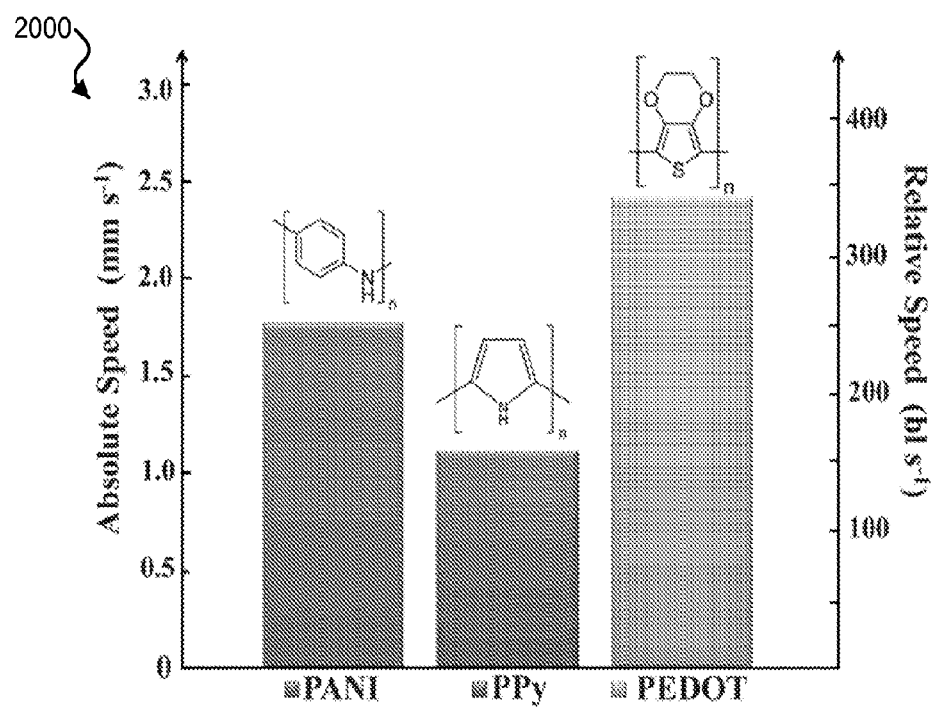
FIG. 20 shows a data plot of the absolute and relative speeds of the exemplary polymer-based bilayer microtubes.

FIG. 20 shows a data plot 2000 of the absolute and relative speeds of the polymer-based bilayer microtubes in a 5% H$_2$O$_2$ solution containing 2.67% (w/v) sodium cholate as surfactant. The exemplary speed data of the data plot 2000 includes speeds of 1120, 2400 and 1700 μm/s (e.g., corresponding to 160, 340 and 240 body lengths/s) for the exemplary PPy/Pt, PEDOT/Pt and PANI/Pt bilayer microengines, respectively. For example, the exemplary differences in the speed can be attributed primarily to the size of the opening diameter. For example, considering the tubular microengine as a cylinder microrod (since the fluid cannot freely flow through microengine because of the oxygen bubbles), the fluid drag coefficient may be the same for the microengines with the same outer diameter and different inner opening diameters; however, the larger inner opening can be coupled with a larger catalytic surface area, hence facilitating the bubble evolution and leading to a faster speed.

Additional implementations showed that the PEDOT/Pt microengines achieved a higher speed in a higher peroxide level (e.g., 10%), e.g., at an average speed of 3350 μm/s (e.g., ~480 body lengths/s). For example, even further acceleration and a speed record (e.g., of ~1400 body lengths/s) was achieved by operating the exemplary PEDOT/Pt microengines at a physiological temperature. The preparation of the exemplary PEDOT-based bilayer microtubes provided more reproducible yields and consistent batch-to-batch morphology and length, e.g., as compared to faster growing PANI-based tubular microengines (e.g., involving a very rapid aniline electropolymerization). The exemplary implementations demonstrated that the PEDOT-based microengines provided the most favorable preparation and propulsion performance.

Figure 21:
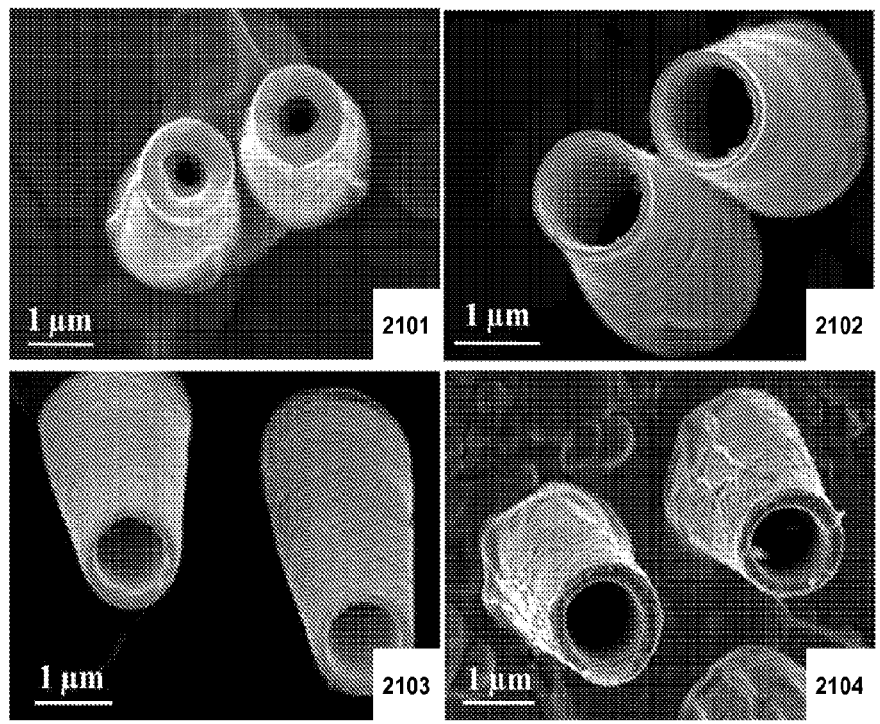
FIG. 21 shows SEM images of PEDOT-based bilayer microtube prepared under different conditions.

FIG. 21 shows SEM images of PEDOT-based bilayer microtube prepared under different conditions. Image 2101 shows an exemplary PEDOT-based bilayer microtube fabricated using 100 mM EDOT and 100 mM SDS. Image 2102 shows an exemplary PEDOT-based bilayer microtube fabricated using 15 mM EDOT and 100 mM sodium dodecyl sulfate. Image 2103 shows an exemplary PEDOT-based bilayer microtube fabricated using 15 mM EDOT and 2 mM SDS. Image 2104 shows an exemplary PEDOT-based bilayer microtube fabricated using only 15 mM EDOT. For example, a 7.5 mM KNO$_3$ supporting electrolyte was used during the electropolymerization process. These exemplary SEM images show different morphological features of PEDOT/Pt tubular microengines, e.g., grown in the different synthesis media.

As indicated from the images of FIG. 21, the monomer concentration and the presence of surfactant in the electropolymerization media can affect the morphology and opening diameter of the resulting polymer microtubes. For example, the effect of the monomer concentration was examined by comparing morphology of the microengines in electrochemical template systems using 15 and 100 mM EDOT (in the presence of 100 mM SDS). The higher monomer concentration led to less uniform, rougher tubular structures with thicker walls (e.g., smaller opening pore), as shown in the images 2101 versus 2102 in FIG. 21. Thus, solvophobic and electrostatic interactions between the pore wall of membrane and reacting species can result in the preferential nucleation and growth of PEDOT onto the pores of the membrane wall, e.g., producing microtube structure with a thicker polymer layer. PEDOT/Pt microtubes prepared using 15 mM EDOT solution were characterized with a smoother more regular surface morphology, along with thinner walls. Such improved microtube structures containing a wider opening pore exhibited faster speeds as compared with PEDOT/Pt microengines prepared in presence of higher monomer concentration.

For example, surfactant effects were also examined for the preparation of PEDOT/Pt microengines using the same monomer concentration. It is noted, for example, that due to the low solubility of EDOT in water, the electropolymerization of EDOT was usually carried out in organic solvents (e.g., which may deteriorate the polycarbonate membrane pores). The surfactant effect upon the PEDOT/Pt microtube structures was investigated using plating solutions containing different surfactant concentrations (e.g., 2 and 100 mM) and 15 mM of the EDOT monomer. As shown in the images 2102 and 2103 in FIG. 21, the film thickness increased from 150 to 100 nm upon decreasing the surfactant concentrations from 100 to 2 mM. For example, without the surfactant, the polymerization created a non-uniform and thicker polymer layer, displayed in the image 2104 of FIG. 21, e.g., which can lead to a smaller inner diameter that greatly hinders the microengine propulsion. The results of these exemplary implementations showed that the most favorable surface morphology was obtained by the polymerization using a low monomer concentration in the presence of proper surfactant (e.g., such as 100 mM concentration). For example, the improvement of the surface quality in presence of surfactant like long-chain alkyl sulfonate groups may be attributed to the decreased oxidation potential of the monomer under the same conditions. Furthermore, for example, the addition of surfactant has improved both the solubility of the monomer and the morphological properties of the polymer because of its dopant anion role in the polymer chain structure. Thus, the surfactant/monomer ratio can also be an important parameter for controlling the surface morphology and physical properties in PEDOT/Pt microtubes for diverse applications.

For example, the nature of the electrolyte was a variable that had an effect on the yield, conductivity and morphology of the polymer microtube structure and growth. The exemplary implementations included comparing the growth of exemplary PEDOT/Pt microtubes in the presence of lithium perchlorate ($LiClO_4$) to the growth in potassium nitrate ($KNO_3$), e.g., in the same aqueous media. For example, the results showed that the polymer growth in $LiClO_4$ was not well repeatable under similar polymerization conditions yielding different lengths. In contrast, for example, the $KNO_3$ electrolyte showed a substantially improved surface morphology, stability and thickness in the PEDOT/Pt microtube structures. For example, charges in the $KNO_3$ electrolyte were consumed more rapidly in the presence of nitrate ions than with chlorate ions, e.g., indicating the faster deposition of the PEDOT doped with nitrate ions. In the presence of $KNO_3$, a homogenous polymer (PEDOT) surface was deposited onto membrane template in a short polymerization time.

Figures 22A, 22B:
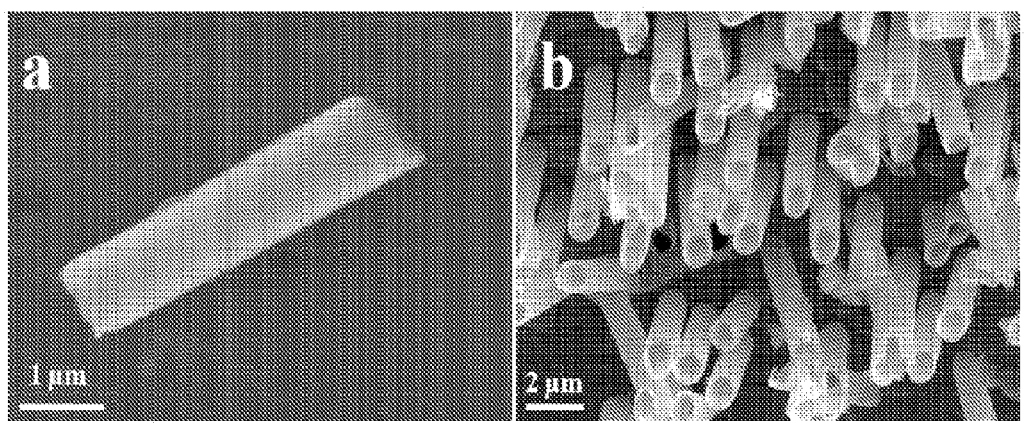
FIGS. 22A and 22B show images of exemplary PEDOT/Pt microtubes with opening diameters of less than 800 nm.

Results of the exemplary implementations showed that the use of membranes with different pore diameters allowed for increased control on the size of the mirotubes. For example, smaller motors can be obtained (e.g., about one half the size of microtubes of 2 μm in diameter and 7-8 μm in length with a membrane with a 1 μm pore size. For example, FIG. 22A shows an SEM image of a single smaller PEDOT/Pt microtube with a length of 4 μm and opening diameters of less than 800 nm (e.g., one half the body length of the previously described 2 μm openings-based template based bilayer microengines). FIG. 22B shows an SEM image of a multiple smaller PEDOT/Pt microtube with a lengths and openings of the size shown in FIG. 22A. The results of the exemplary implementations showed that the smaller microengines can also achieve a very high speed. For example, the smaller microengine was shown to move at a speed of 325 μm/s in a 4% $H_2O_2$ (e.g., containing 5% sodium cholate), e.g., corresponding to a relative speed of over 80 body lengths/s.

Figure 23:
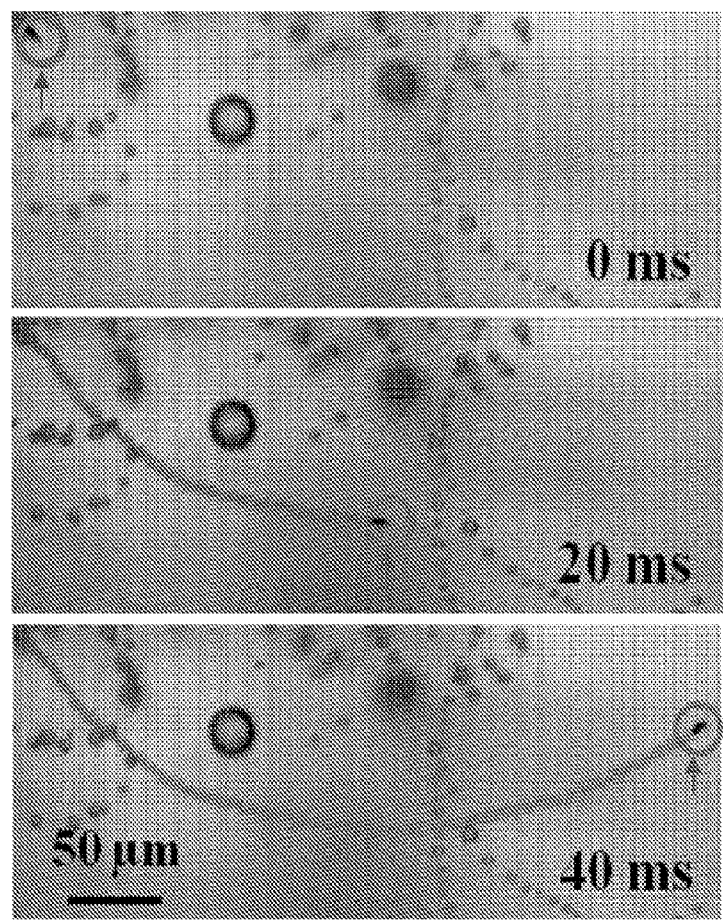
FIG. 23 shows images of the propulsion of exemplary PEDOT/Pt microengines in a fuel solution at a physiological temperature.

For example, the temperature can also influence the speed of catalytic micro/nanomotors, e.g., through its effect on the electrochemical reactivity of hydrogen peroxide decomposition. A similar phenomenon was observed in the exemplary implementations of the disclosed polymer-based microtubes. FIG. 23 shows images demonstrating the propulsion (over 1400 body lengths/s) of exemplary PEDOT/Pt microengines in 10% $H_2O_2$ and 5% sodium cholate surfactant in physiological temperature of 37° C. over a 40 ms period. For example, at the physiological temperature of 37° C., the described template-based PEDOT/Pt microengines can achieve a speed of over 1400 body lengths/s (e.g., 10 mm/s in absolute speed), e.g., as compared to around 500 body lengths/s in room temperature. For example, under the same conditions, PANI/Pt based microengines can also achieve a speed of over 730 body lengths/s (e.g., compared to 350 body lengths/s in room temperature).

Figure 24:
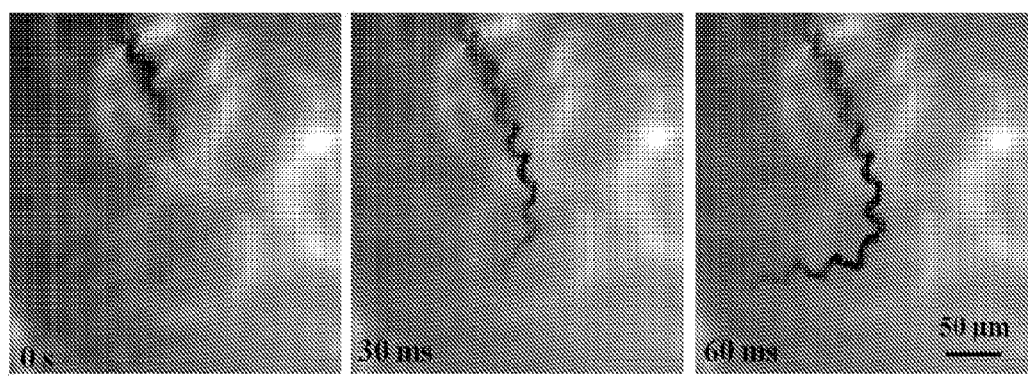
FIG. 24 shows images of propulsion of an exemplary PANI/Pt microengine at room temperature in a fuel solution with hydrazine.

For example, in addition to increasing temperature, adding hydrazine can also lead to a dramatic increase in the speed of disclosed catalytic tubular microengines. FIG. 24 shows images of propulsion of an exemplary PANI/Pt microengine at around 5 mm/s (e.g, corresponding to around 700 body lengths/s) at room temperature in a 10% $H_2O_2$ solution with 0.25% hydrazine. For example, the propulsion of the exemplary platinum-based microengines using hydrazine fuel alone (without any hydrogen peroxide) was also been observed. For example, the motion of these exemplary platinum-based microengines in a 0.1% hydrazine solution produced $N_2$ bubbles; yet, their propulsion was observed to be short-lived (e.g., 1-2 seconds) in this exemplary implementation.

The exemplary implementations also included utilizing alternative catalytic metals other than platinum in the inner catalytic layer of tubular microengines. For example, silver can be implemented as a catalyst for hydrogen peroxide decomposition, and can therefore be used as the inner catalytic layer of the disclosed microengines. FIG. 25A shows an image of an exemplary PPy/Ag bilayer microengine moving efficiently at a speed of 500 μm/s in the presence of 15% hydrogen peroxide and 3% sodium cholate surfactant. For example, the silver layer can be partially dissolved in hydrogen peroxide. For example, the results showed that the speed of the exemplary PPy/Ag microengine was slower than of the platinum-based polymer microtubes (e.g., under same conditions). However, the exemplary PPy/Ag bilayer microengines were shown to still propel at fast speeds, e.g., considering the relative speed of more than 70 body lengths/s, which is substantially greater speeds that speeds of conventional rolled-up platinum-based microengines. The propulsion of the exemplary PPy/Ag microtubes was observed for over 40 min without considerable speed variations.

Magnetic guidance and control can be engineered within the catalytic micro/nanomotors. In some examples, trilayer microengines can be configured with the addition of an inner nickel layer between the outer polymer layer and the inner catalytic layer that can provide magnetically-guided propulsion. This exemplary configuration can include preparation using a three-step electrodeposition process, e.g., such as including an additional electrodeposition process within the process described in FIG. 1A. In other examples, a Pt/Ni alloy inner catalytic layer that also includes magnetic properties response to an applied magnetic field can be employed. For example, instead of a separate platinum inner layer and a separate nickel intermediate layer, the disclosed membrane template electrodeposition technology can include fabrication of a Pt/Ni alloy inner layer that provides simultaneously both the catalytic activity and desired magnetic navigation of the fabricated polymer/Pt—Ni microtube engine. FIG. 25B shows an image of the propulsion of an exemplary PPy/Pt—Ni-alloy microengine in a 10% hydrogen peroxide solution. The exemplary PPy/alloy microengine displayed efficient propulsion at a speed of 470 μm/s (e.g., 67 body lengths/s).

The disclosed nano/microscale motors can also include microtube engine structures having an inner palladium (Pd) or iridium (Ir) catalytic layers. However, for example, it is noted that it can be difficult to deposit a defined Pd or Ir layer within the polymer layer. For example, Pd and Ir can grow on the top of the tube and block the pores, e.g., which can result in eliminating the tubular bubble propulsion.

The disclosed technology can include nano/micromotors having biocatalytic layers (e.g., based on immobilized catalase, instead of electrocatalytic metals) for propelling the exemplary peroxide-driven nano/microscale motors. For example, a gold inner layer electrodeposited inside the outer polymeric tube layer can be used to immobilize the catalase biocatalyst. For example, template electrodeposition of the polymer-Au microtube can result in a very rough surface (shown in FIG. 26A) for immobilizing large amounts of the enzyme. FIG. 26A shows an SEM image of PPy/Au$_{rough}$ bilayer micro tubular microengine. FIG. 26B shows an image of the biocatalytic propulsion of an exemplary PPy/Au-catalase microtube engine in a fuel fluid (e.g., 0.5% $H_2O_2$ and 2% sodium cholate). As illustrated in FIG. 26B, the resulting biocatalytic bilayer microengines propel favorably in the presence of a low peroxide level (e.g., the 0.5% $H_2O_2$ fuel) at a speed of 8 body lengths/s.

Figure 27:
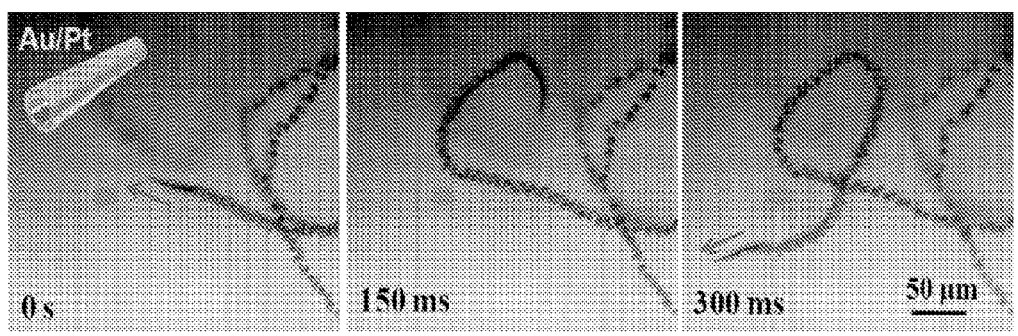
FIG. 27 shows images demonstrating the propulsion of an exemplary Au/Pt bimetallic microtube engine in a fuel fluid.

Also for example, the disclosed nano/microscale motors can include an outer gold layer to enable functionalization of an exemplary nano/microtube structure, which can also provide excellent biocompatibility. FIG. 27 shows images demonstrating the propulsion of an exemplary Au/Pt bimetallic microtube engine in a fuel fluid (e.g., 5% $H_2O_2$ and 2% sodium cholate). As shown in FIG. 27, the exemplary Au/Pt bimetallic microengines can propel rapidly at a speed of 1.5 mm/s in a 10% $H_2O_2$ and 2.67% sodium cholate solution.

Figure 28:
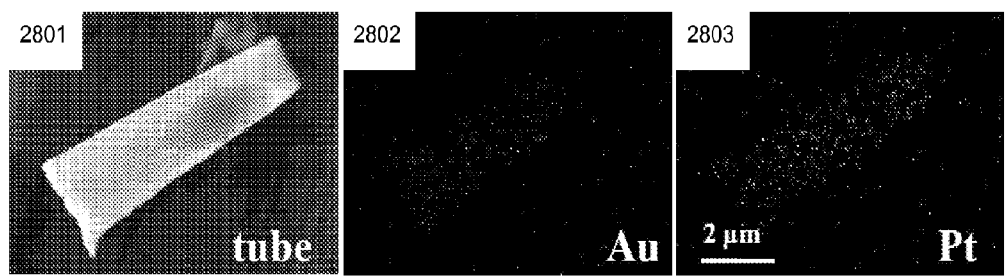
FIG. 28 also shows SEM images and EDX mapping data of exemplary Au/Pt bimetallic microtube engine.

The exemplary Au/Pt bimetallic microtube engines couple the advantages of an outer Au layer able to be functionalized with the effective catalytic activity of the inner Pt layer. The described template synthesis techniques of the disclosed technology can be applied to produce these exemplary Au/Pt bilayer microengines. For example, the Au outer layer can be electrodeposited from a Au plating solution containing 0.1 M $NaNO_3$ using DMSO as an electrolyte (e.g., without addition of any other surfactants), followed by a subsequent deposition of an inner platinum layer. In some examples, the resulting gold outer surface can be relatively rough (e.g., as shown in image 2801 of FIG. 28). For example, the rough surface may be attributed to the interaction of DMSO and the polycarbonate membrane. For example, DMSO may slowly dissolve the polycarbonate membranes, making the pores shrink as the microtube is growing. This can also result in a lower yield of these viable microtubes with a non-uniform, rough outer layer. FIG. 28 also shows exemplary EDX mapping data (e.g., images 2802 and 2803) that confirm the presence of the gold and platinum layers.

The electropolymerization conditions of the disclosed fabrication techniques have been shown to affect the morphology and propulsion behavior. For example, the morphology of the conducting polymer microtube can be influenced by the nature and concentration of monomer and of the supporting electrolyte, as well as by the surfactant present, as described. For example, the disclosed nanomotors and micromotors can be implemented in advanced sensor systems of diverse chemicals, e.g., such as biomaterials, hydrogen peroxide or methanol fuel cell systems. Moreover, for example, the disclosed conducting polymer/metal microtubes are inexpensive and versatile and can be readily modified by the use of a wide range of molecules that can be entrapped or used as dopants. Polymers with different functional groups (e.g., such as —OH or —COOH) can be chosen as the outer layer for different applications, hence facilitating different surface functionalization processes. Also for example, mixed polymers (e.g., co-polymers with more than one type of functional group) can be selected as the outer layers material, e.g., which can also facilitate different surface functionalization processes. These exemplary properties and advantages of the disclosed polymer-based tubular microengines can permit their implementations in diverse biomedical and industrial applications.

In another aspect, the disclosed technology can include exemplary nano/microtube structures can be configured to propel in a fluid by a gas-bubble propulsion mechanism based on the chemical reactions of inner surface material of the nano/microengine structure with basic species in the fluid.

Exemplary aluminum-based microtube engines (e.g., PANI/Al bilayer microtubes) can be fabricated using the present membrane-template electrodeposition fabrication techniques to move by hydrogen-bubble propulsion in basic or alkaline fluid environment. An exemplary basic-driven microtube engine can be structured to include a large opening and a small opening that are on opposite ends of the microtube, in which the microtube includes a tube body connecting the openings and has a cross section spatially reducing in size along a longitudinal direction from the large opening to the small opening. The microtube engine can include a layered wall in which an inner layer can include a chemically-reactive material (e.g., aluminum (Al)) exposed to the basic fluid. For example, the polymer/aluminum bilayer microtube engines can undergo effective autonomous motion in the basic fluid environment without any additional chemical fuel. The propulsion in the basic fluid can be driven by continuous thrust of hydrogen bubbles generated by the spontaneous redox reactions occurring at the inner layer surface (e.g., the inner Al layer). The reaction here is 2 Al (s)+2OH$^-$ (aq)→2 AlO$_2^-$ (aq)+H$_2$ (g). For example, when the exemplary PANI/Al bilayer microengines are immersed in a strongly basic medium, a spontaneous redox reaction, e.g., involving the Al oxidation along with generation of hydrogen bubbles, occurs on their inner Al surface. Other materials that can be employed as the inner layer material of the base-driven microtube engines, e.g., which include metals (e.g., Na, K, Ca, Mg, or Zn).

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method of fabricating one or more microtubes, comprising:
    depositing a first layer on a template that has one or more holes of a desired hole geometry to form a tube of the first layer in each hole;
    depositing a second layer over the first layer inside each hole of the template to form a bilayer microtube formed of the first and second layers inside each hole; and
    separating the template from each bilayer microtube;
    wherein the first layer comprises a polymer material;
    wherein the polymer material comprises one of polypyrrole (PPy) and poly(3,4-ethylenedioxythiophene) (PEDOT).

2. The method of claim 1, wherein the second layer comprises a material that is reactive with a fuel or is a catalyst of a fuel.

3. The method of claim 2, wherein the material that is reactive with a fuel or is a catalyst of a fuel comprises a conductive metal.

4. The method of claim 2, wherein the material that is a catalyst of a fuel comprises platinum.

5. A method of fabricating one or more microtubes, comprising:
    depositing a first layer on a template that has one or more holes of a desired hole geometry to form a tube of the first layer in each hole;
    depositing a second layer over the first layer inside each hole of the template to form a bilayer microtube formed of the first and second layers inside each hole; and
    separating the template from each bilayer microtube;
    wherein the template comprises cyclopore polycarbonated membrane.

6. The method of claim 5, wherein the cyclopore polycarbonated membrane comprises an asymmetrical, conically-shaped pore structure.

7. The method of claim 6, wherein the asymmetrical conically-shaped pore structure comprises different cone angles.

8. A method of fabricating one or more microtubes, comprising:
    depositing a first layer on a template that has one or more holes of a desired hole geometry to form a tube of the first layer in each hole;
    depositing a second layer over the first layer inside each hole of the template to form a bilayer microtube formed of the first and second layers inside each hole; and
    separating the template from each bilayer microtube;
    wherein the microtube comprises a self-propulsion.

9. The method of claim 8, wherein several hundreds of microtube body lengths per second speed is achieved.

10. The method of claim 1, the microtube comprises a fuel based microtube.

11. The method of claim 10, wherein the fuel based microtube uses a 0.2%-30% concentration hydrogen peroxide fuel.

12. The method of claim 8, wherein the microtube is fabricated to different diameters and lengths.

13. The method of claim 1, wherein the separating is performed by dissolving the template.

14. The method of claim 13, wherein the intermediate second layer comprises a ferromagnetic material.

15. The method of claim 14, wherein the ferromagnetic material comprises nickel, iron or cobalt.

16. The method of claim 13, wherein the third layer comprises a material that is reactive with a fuel or a catalyst of a fuel.

17. The method of claim 16, wherein the material that is reactive with a fuel or a catalyst of a fuel comprises a conductive material.

18. The method of claim 16, wherein the material that is reactive with a fuel or a catalyst of a fuel a fuel comprises platinum.

19. The method of claim 13, wherein the dissolving is performed using methylene chloride.

20. The method of claim 1, wherein the depositing the second layer includes depositing the second layer by using a galvanostatic deposition.

21. A method of fabricating one or more microtubes, comprising:
    depositing a first layer on a template that has one or more holes to form a tube of the first layer in each hole;
    depositing an intermediate second layer over the first layer inside each hole;
    depositing a third layer over the intermediate second layer inside each hold to form a trilayer microtube formed of the first, intermediate second, and third layers inside each hole; and
    separating the template from each trilayer microtube;
    wherein the polymer material comprises one of polypyrrole (PPy) and poly(3,4-ethylenedioxythiophene) (PEDOT).

22. The method of claim 21, wherein the separating is performed by dissolving the template.

23. The method of claim 22, wherein the dissolving is performed using methylene chloride.

24. The method of claim 21, wherein the depositing the second layer includes depositing the second layer by using a galvanostatic deposition.

* * * * *